(12) United States Patent
Stinson

(10) Patent No.: US 6,997,948 B2
(45) Date of Patent: *Feb. 14, 2006

(54) BIOABSORBABLE SELF-EXPANDING STENT

(75) Inventor: Jonathan S. Stinson, Plymouth, MN (US)

(73) Assignee: Boston Scientific SciMed, Inc., Maple Grove, MN (US)

( * ) Notice: Subject to any disclaimer, the term of this patent is extended or adjusted under 35 U.S.C. 154(b) by 2 days.

This patent is subject to a terminal disclaimer.

(21) Appl. No.: 10/823,128

(22) Filed: Apr. 13, 2004

(65) Prior Publication Data

US 2004/0193241 A1   Sep. 30, 2004

Related U.S. Application Data

(62) Division of application No. 09/843,425, filed on Apr. 25, 2001, now Pat. No. 6,719,934, which is a division of application No. 08/904,467, filed on Aug. 1, 1997, now Pat. No. 6,245,103.

(51) Int. Cl.
*A61F 2/06* (2006.01)
*D02G 3/44* (2006.01)

(52) U.S. Cl. .................... 623/1.38; 623/1.15; 264/40.1
(58) Field of Classification Search ...... 623/1.11–1.54; 264/40.1, 103, 235
See application file for complete search history.

(56) References Cited

U.S. PATENT DOCUMENTS

| | | | | |
|---|---|---|---|---|
| 4,954,126 A | * | 9/1990 | Wallsten | 600/36 |
| 5,527,337 A | * | 6/1996 | Stack et al. | 606/198 |
| 5,700,901 A | * | 12/1997 | Hurst et al. | 528/354 |
| 5,997,468 A | * | 12/1999 | Wolff et al. | 600/36 |
| 6,245,103 B1 | * | 6/2001 | Stinson | 623/1.22 |
| 6,719,934 B1 | * | 4/2004 | Stinson | 264/40.1 |

* cited by examiner

*Primary Examiner*—Suzette J-J Gherbi
(74) *Attorney, Agent, or Firm*—Larkin Hoffman Daly & Lindgren Ltd.; Frederick W. Niebuhr, Esq.

(57) ABSTRACT

A self-expanding stent formed from helically wound and braided filaments of bioabsorbable polymers such as PLA, PLLA, PDLA, and PGA.

30 Claims, 16 Drawing Sheets

BIOABSORBABLE SELF-EXPANDING STENT

This is a divisional of application Ser. No. 09/843,425 (now U.S. Pat. No. 6,719,934) entitled "Process For Making Bioabsorbable Self-Expanding Stent," filed Apr. 25, 2001 which is a divisional of application Ser. No. 08/904,467 entitled "Bioabsorbable Self-Expanding Stent," filed Aug. 1, 1997 (now U.S. Pat. No. 6,245,103).

BACKGROUND OF THE INVENTION

The present invention relates generally to implantable, radially expandable medical prostheses which are frequently referred to as stents. In particular, the present invention is a bioabsorbable self-expanding stent.

Self-expanding medical prostheses frequently referred to as stents are well known and commercially available. They are; for example, disclosed generally in the Wallsten U.S. Pat. No. 4,655,771, the Wallsten et al. U.S. Pat. No. 5,061,275 and in Hachtmann et al., U.S. Pat. No. 5,645,559. Devices are used within body vessels of humans for a variety of medical applications. Examples include intravascular stents for treating stenoses, stents for maintaining openings in the urinary, biliary, tracheobronchial, esophageal, and renal tracts, and vena cava filters.

A delivery device which retains the stent in its compressed state is used to deliver the stent to a treatment site through vessels in the body. The flexible nature and reduced radius of the compressed stent enables it to be delivered through relatively small and curved vessels. In percutaneous transluminal angioplasty, an implantable endoprosthesis is introduced through a small percutaneous puncture site, airway, or port and is passed through various body vessels to the treatment site. After the stent is positioned at the treatment site, the delivery device is actuated to release the stent, thereby allowing the stent to self-expand within the body vessel. The delivery device is then detached from the stent and removed from the patient. The stent remains in the vessel at the treatment site as an implant.

Stents must exhibit a relatively high degree of biocompatibility since they are implanted in the body. An endoprosthesis may be delivered into a body lumen on or within a surgical delivery system such as delivery devices shown in U.S. Pat. Nos. 4,954,126 and 5,026,377. Preferred delivery devices for the present invention include U.S. Pat. Nos. 4,954,126; 5,026,377. Suitable materials for use with such delivery devices are described in U.S. patent application Ser. No. 08/833,639, filed Apr. 8, 1997.

Commonly used materials for known stent filaments include Elgiloy® and Phynox® metal spring alloys. Other metallic materials than can be used for self-expanding stent filaments are 316 stainless steel, MP35N alloy, and superelastic Nitinol nickel-titanium. Another self-expanding stent, available from Schneider (USA) Inc. of Minneapolis, Minn., has a radiopaque clad composite structure such as shown in U.S. Pat. No. 5,630,840 to Mayer. Self-expanding stents can be made of a Titanium Alloy as described in U.S. patent application Ser. No. 08/598,751, filed Feb. 8, 1996.

The strength and modulus of elasticity of the filaments forming the stents are also important characteristics. Elgiloy®, Phynox®, MP35N and stainless steel are all high strength and high modulus metals. Nitinol has relatively low strength and modulus.

The implantation of an intraluminal stent will preferably cause a generally reduced amount of acute and chronic trauma to the luminal wall while performing its function. A stent that applies a gentle radial force against the wall and that is compliant and flexible with lumen movements is preferred for use in diseased, weakened, or brittle lumens. The stent will preferably be capable of withstanding radially occlusive pressure from tumors, plaque, and luminal recoil and remodeling.

There remains a continuing need for self-expanding stents with particular characteristics for use in various medical indications. Stents are needed for implantation in an ever growing list of vessels in the body. Different physiological environments are encountered and it is recognized that there is no universally acceptable set of stent characteristics.

A need exists for a stent which has self expanding characteristics, but which is bioabsorbable. A surgical implant such as a stent endoprosthesis must be made of a non-toxic, biocompatible material in order to minimize the foreign-body response of the host tissue. The implant must also have sufficient structural strength, biostability, size, and durability to withstand the conditions and confinement in a body lumen.

All documents cited herein, including the foregoing, are incorporated herein by reference in their entireties for all purposes.

SUMMARY OF THE INVENTION

The present invention is an improved implantable medical device comprised of a tubular, radially compressible, axially flexible and radially self-expandable structure including elongate filaments formed in a braid-like configuration. The filaments consist of a bioabsorbable polymer which exhibits a relatively high degree of biocompatibility.

Briefly, self-expanding stents of the present invention are formed from a number of resilient filaments which are helically wound and interwoven in a braided configuration. The stents assume a substantially tubular form in their unloaded or expanded state when they are not subjected to external forces. When subjected to inwardly directed radial forces the stents are forced into a reduced-radius and extended-length loaded or compressed state. The stents are generally characterized by a longitudinal shortening upon radial expansion.

In one preferred embodiment, the device is a stent which substantially consists of a plurality of elongate polylactide bioabsorbable polymer filaments, helically wound and interwoven in a braided configuration to form a tube. Bioabsorbable implantable endoprostheses such as stents, stent-grafts, grafts, filters, occlusive devices, and valves may be made of poly(alpha-hydroxy acid) such as poly-L-lactide (PLLA); poly-D-lactide (PDLA), polyglycolide (PGA), polydioxanone, polycaprolactone, polygluconate, polylactic acid-polyethylene oxide copolymers, modified cellulose, collagen, poly(hydroxybutyrate), polyanhydride, polyphosphoester, poly(amino-acids), or related copolymers materials, each of which have a characteristic degradation rate in the body. For example, PGA and polydioxanone are relatively fast-bioabsorbing materials (weeks to months) and PLA and polycaprolactone are a relatively slow-bioabsorbing material (months to years).

A stent constructed of a bioabsorbable polymer provides certain advantages relative to metal stents such as natural decomposition into non-toxic chemical species over a period of time. Also, bioabsorbable polymeric stents may be manufactured at relatively low manufacturing costs since vacuum heat treatment and chemical cleaning commonly used in metal stent manufacturing are not required.

The present invention includes a method of designing and manufacturing an improved braided bioabsorbable stent which is different from practices used to make braided metal wire stents. The method involves selecting a specific bioabsorbable polymer based on a desired stent functional absorption time and stent radial force. The stent functional absorption time is the time period within which the stent retains at least 80% of its original radial strength. The stent is made by first selecting a braid design from the invention and making two different annealed stents. Radial force and dimensional test results from the two stents are used to develop a nearly linear mathematical equation to determine the parameters to meet the design goals. This method advantageously limits costly and time consuming trial and error to arrive at the optimum design.

Bioabsorbable polymer stents are radiolucent and the mechanical properties of the polymers are generally lower than structural metal alloys. Bioabsorbable stents may require radiopaque markers and may have a larger profile on a delivery catheter and in a body lumen to compensate for the lower material properties.

Bioabsorbable PLLA and PGA material are degraded in vivo through hydrolytic chain scission to lactic acid and glycolic acid, respectively, which in turn is converted to $CO_2$ and then eliminated from the body by respiration. Heterogeneous degradation of semicrystalline polymers occurs due to the fact that such materials have amorphous and crystalline regions. Degradation occurs more rapidly at amorphous regions than at crystalline regions. This results in the product decreasing in strength faster than it decreases in mass. Totally amorphous, cross-linked polyesters show a more linear decrease in strength with mass over time as compared to a material with crystalline and amorphous regions. Degradation time may be affected by variations in chemical composition and polymer chain structures, and material processing.

PLA monofilaments may be produced by a process involving seven general steps as summarized herein. First, a polymer formed of poly-L-lactic acid is brought to an elevated temperature above the melting point, preferably 210°–230° C. Second, the material is then extruded at the elevated temperature into a continuous fiber, by a conventional process, at a rate about of three to four feet per minute. Third, the continuous fiber is then cooled to cause nucleation. The cooling is preferably performed by passing the fiber through a nucleation bath of water. Fourth, the material then passes through a first puller, which runs at about the same speed as the extruder, and places the material under slight tension. Fifth, the fiber is then heated to a temperature between about 60° C. and about 90° C. (preferably 70° C.) as it passes through a heated oven. To perform annealing, the oven can be designed to be quite long and heated near the end, so that the orientation and annealing take place in the same oven. Alternatively, a separate oven can be placed directly after the orientation oven. The annealing step heats the fibers to a range of about 65° C. to about 90° C., preferably closer to 90° C. Sixth, while being heated in the orientation oven and the annealing oven, the fiber is drawn between the first puller located before the orientation oven and a second puller located after the annealing oven (if a separate oven). The material is drawn at a draw ratio of between about 5 to about 9, preferably between about 6 and about 8. Draw ratio describes the extension in length resulting from polymer extrusion or drawing. Quantitatively, the drawing ratio is a unitless value equal to the extruded or drawn length divided by the original length. Maintaining tension through the annealing step prevents shrinkage in later use. The second puller, located at the exit of the oven, runs at an increased speed necessary to provide the desired draw ratio. As the fiber exits the oven and passes through the second puller the tension is immediately released before the material cools. Seventh, finally, the fiber is collected onto spools of desired lengths.

Strength of the filaments generally increases with draw ratio and with lower draw temperatures. A draw ratio of between 5 and 9 is preferred. PLA is generally amorphous because of the material's slow crystallization kinetics. Very slow cooling after drawing of the filament or use of a nucleating agent will cause crystallization. However, the material may be annealed at temperatures above about 60° C. to cause crystallization, and generally, the strength decreases slightly and the modulus increases. Annealing is preferably performed after drawing to release residual stresses and to homogenize the surface to center variations in structure. Annealing will preferably be performed at a temperature of between about 60° C. and 150° C. for a period of time between about 5 and 120 minutes. Reference is made to *Enhancement of the Mechanical properties of polylactides by solid-state extrusion*, W. Weiler and S. Gogolewski, Biomaterials 1996, Vol 17 No. 5, pp. 529–535; and *Deformation Characteristics of a Bioabsorbable Intravascular Stent*, Investigative Radiology, December 1992, C. Mauli, Agrawal, Ph.D., P. E., H. G. Clark, Ph.D., pp. 1020–1024. It is generally preferred in accordance with this invention that the annealed bioabsorbable filament has a substantially homogeneous cross-section, in other words, that it has a substantially solid cross-section without substantial variations between the center and the surface of the filament.

Mechanical properties generally increase with increasing molecular weight. For instance, the strength and modulus of PLA generally increases with increasing molecular weight. Degradation time generally decreases with decreasing initial molecular weight (i.e., a stent made of a low molecular weight polymer would be bioabsorbed before a stent made of a high molecular weight polymer). Low molecular weight PLA is generally more susceptible to thermo-oxidative degradation than high molecular weight grades, so an optimum molecular weight range should be selected to balance properties, degradation time, and stability. The molecular weight and mechanical properties of the material generally decreases as degradation progresses. PLA generally has a degradation time greater than 1 year. Ethylene oxide sterilization process (EtO) is a preferred method of sterilization. PLA has a glass transition temperature of about 60° C., so care must be taken not to store products in environments where high temperature exposure may result in dimensional distortion.

PLA, PLLA, PDLA and PGA include tensile strengths of from about 40 thousands of pounds per square inch (ksi) to about 120 ksi; a tensile strength of 80 ksi is typical; and a preferred tensile strength of from about 60 ksi to about 120 ksi. Polydioxanone, polycaprolactone, and polygluconate include tensile strengths of from about 15 ksi to about 60 ksi; a tensile strength of 35 ksi is typical; and a preferred tensile strength of from about 25 ksi to about 45 ksi.

PLA, PLLA, PDLA and PGA include tensile modulus of from about 400,000 pounds per square inch (psi) to about 2,000,000 psi; a tensile modulus of 900,000 psi is typical; and a preferred tensile modulus of from about 700,000 psi to about 1,200,000 psi. Polydioxanone, polycaprolactone, and polygluconate include tensile modulus of from about 200,000 psi to about 700,000 psi; a tensile modulus of 450,000 psi is typical; and a preferred tensile modulus of from about 350,000 psi to about 550,000 psi.

PLLA filament has a much lower tensile strength and tensile modulus than, for example, Elgiloy® metal alloy wire which may be used to make raided stents. The tensile strength of PLLA is about 22% of the tensile strength of Elgiloy®. The tensile modulus of PLLA is about 3% of the tensile modulus of Elgiloy®. Stent mechanical properties and self-expansion are directly proportional to tensile modulus of the material. As a result, a PLLA filament braided stent made to the same design as the metal stent has low mechanical properties and would not be functional. The invention advantageously provides polymeric braided stents with radial strength similar to metal stents and the required mechanical properties capable of bracing open endoluminal strictures.

A bioabsorbable PLLA braided tubular stent changes size when constrained onto a catheter delivery system and when deployed. A deployed PLLA stent is generally longer in length and smaller in diameter than a PLLA stent prior to loading. For example, PLLA stents that were initially 30 mm long with external diameters of about 10.7 mm had deployed lengths of about 90 mm with diameters of about 6.3 mm.

In comparison, a metal self-expanding stent generally has about the same dimensions before loading and after deployment. For metal stents, if it is known that the patient has a 9 mm diameter vessel, then a 10 mm metal stent (stent is intentionally oversized by about 1 mm) is loaded onto the delivery system for implantation. This rule is not applicable for a polymer stent because more oversizing is necessary.

The present invention provides improved polymeric stents and a method for designing and producing the improved polymeric stents whereby a polymeric stent of a certain size may be produced, loaded on the delivery system, and upon deployment will yield desired implant dimensions and have desired mechanical properties.

The present invention advantageously provides a bioabsorbable PLLA braided stent of a desired implant size, and provides a method to make the stent at a particular diameter (A), anneal the stent at a smaller diameter (B), and deploy the stent from a delivery system of diameter (C) whereby the stent will be "programmed" to self-expand to a desired implant diameter (D). The relationship between the diameters is A>B>D>C.

In sum, the invention relates to a bioabsorbable implantable stent having G tubular, radially compressible and self-expandable braided and annealed structure including a first set of between 5 and 18 filaments, each of which extends in a helix configuration along a center line of the stent and having a first common direction of winding. A second set of filaments of the same number as the first set, each extend in a helix configuration along a center line of the stent and having a second common direction of winding. The second set of filaments cross the first set of filaments at an axially directed angle of between about 120 and about 150 degrees when in a first free radially expanded state after being annealed, but before being loaded on a delivery device so as to form a plurality of interstices between filaments. The term "free state" is used when no externally applied forces are acting on the device, for example, when the device is resting on a table. Each filament includes PLLA, PDLA, PGA, or combinations thereof and have a substantially solid and substantially uniform cross-section, a tensile strength of from about 40 ksi to about 120 ksi, a tensile modulus of from about 400,000 psi to about 2,000,000 psi, and an average diameter of from about 0.15 mm to about 0.6 mm. The first set of filaments and second set of filaments act upon one another to create an outwardly directed radial force sufficient to implant the stent in a body vessel upon deployment from a delivery device. The stent may have a second free radially expanded state after being loaded and then released from a deployment device and the first and second sets of filaments cross at an axially directed angle of between about 80 and about 145 degrees when in the second free radially expanded state. The second sets of filaments may crisscross at an axially directed angle of between about 90 and about 100 degrees when in the second free radially expanded state, and a second free state diameter of from about 3 mm to about 6 mm. The axially directed angle may be between about 110 degrees and about 120 degrees when in the second free radially expanded state. The stent may have an outside diameter when in the second free radially expanded state and the stent exerts an outwardly directed radial force at one half of the outside diameter of from about 40 grams to about 300 grams. The stent may have an implanted state after being loaded, released from a deployment device into a body vessel, and then implanted in the body vessel, with the first and second sets of filaments crossing at an axially directed angle of between about 95 and 105 degrees when the stent is in the implanted state. The stent may be radially constrained to half of its free diameter and the radial force, RF, exerted by the device, in grams, as a function of annealed diameter, D, in mm, is about RIF=−15D+491±20. The stent may be annealed at a temperature of from about 60° C. to about 180° C. for a period of time of from about 5 minutes to about 120 minutes. The stent may be annealed at a temperature of from about 130° C. to about 150° C. for a period of time of from about 10 minutes to about 20 minutes. The braid may be annealed to yield a crossing angle of from about 130 degrees to about 150 degrees. The stent may be further disposed in a stent delivery device and the filaments have a crossing angle of from about 30 degrees to about 120 degrees. The stent may be deployed from a delivery system into a body lumen and the filaments have a crossing angle of from about 70 degrees to about 130 degrees. The stent may provide structural integrity to a body lumen for less than about 3 years. The stent may further include polydioxanone, polycaprolactone, polygluconate, polylactic acid-polyethylene oxide copolymers, modified cellulose, collagen, poly (hydroxybutyrate), polyanhydride, polyphosphoester, poly (amino acids) and combinations thereof. The filaments may be mono-filament or multi-filament. The stent may substantially degrade in vivo in from about 1 year to about 2 years. "Substantially degrade" means that the stent has lost at least 50% of its structural strength. It is preferable that the stent lose about 100% of its structural strength. The filaments may include polyglycolide and the stent may substantially degrades in vivo in a time of from about 3 months to about 1 year. The filaments may further include polygluconate, polydioxanone, or combinations thereof and the stent may substantially degrade in vivo in from about 1 week to about 3 months. The stent may have at least one end of diminishing diameter so as to function as a filter. The filaments may be substantially homogeneous in cross section and length. The filaments may have a tensile modulus of from about 400,000 psi to about 1,200,000 psi. The filaments may have a tensile modulus of from about 700,000 psi to about 1,200,000 psi. The stent may includes a plurality of the filaments helically wound and interwoven in a braided configuration to form a tube.

The invention also relates to a method of using an implantable endoprosthesis including: providing a tubular, radially compressible, axially flexible, and radially self-expandable braided and annealed structure. The structure including from about 10 to about 36 elongate filaments. The filament comprising PLLA, PDLA, PGA, and combinations thereof. Each filament having a substantially uniform cross-section, a tensile strength of from about 40 ksi to about 120 ksi, and a tensile modulus of from about 400,000 psi to about 2,000,000 psi. The filaments disposed at an angle of from about 130 degrees to about 150 degrees in a free state, each filament having an average diameter of from about 0.15 mm to about 0.6 mm, and the stent having a radial force at one-half diameter of from about 40 grams to about 300 grams. The annealed structure having a first diameter; disposing the structure into a delivery system at a second diameter smaller than the first diameter; inserting the delivery system and endoprosthesis in a body lumen; deploying the endoprosthesis from the delivery system into the body lumen to a third diameter smaller than the first; and allowing the endoprosthesis to self expand in the body lumen to a fourth diameter greater than the third diameter.

The invention also relates to a method for treating a site within a vessel of a patient, including: providing a biocompatible medical device, including a tubular and axially flexible braid-like annealed structure at a first diameter which is radially self-expandable between a compressed state and an expanded state and which includes from about 10 to about 36 elongate filaments. The filaments include PLLA, PDLA, PGA, and combinations thereof. Each filament has a substantially uniform cross-section, a tensile strength of from about 40 ksi to about 120 ksi, and a tensile modulus of from about 400,000 psi to about 2,000,000 psi; Providing a delivery system with the medical device positioned on a portion of the delivery system in the compressed state at a second diameter smaller than the first diameter; Inserting the portion of the delivery system with the medical device into the patient's vessel at a location spaced from the treatment site, and manipulating the delivery system to advance the medical device through the vessel, to the treatment site; Deploying the medical device from the delivery system. The medical device being deployed at a third diameter smaller than the original free diameter and allowing the medical device to self-expand within the vessel; and Removing the delivery system from the patient with the medical device remaining in the expanded state and supporting the vessel.

The invention also relates to a bioabsorbable implantable device made from the process including providing a plurality of elongate filaments including PLLA, PDLA, PGA, and combinations thereof; braiding the filaments on a first mandrel to form a tubular, radially compressible, axially flexible, and radially self-expandable device. The device having a first diameter of from about 2 mm to about 10 mm larger than the final implanted device diameter; and annealing the device on a second mandrel having a second diameter smaller than the first diameter. The second mandrel diameter adapted to be computed from a linear equation relating radial force to annealed stent diameter. The equation being derived from measured radial force and measured annealed stent diameter data from two stent prototypes made on two anneal mandrel diameters and deployed from a device delivery system. Each filament may have a substantially uniform cross-section, a tensile strength of from about 40 ksi to about 120 ksi, and a tensile modulus of from about 400,000 psi to about 2,000,000 psi. Annealing may cause the device to radially shrink.

The invention also relates to a method of manufacturing a stent including: providing from about 10 to about 36 filaments consisting essentially of poly (alpha-hydroxy acid). The filaments have an average diameter from about 0.15 mm to about 0.60 mm; braiding the filaments at a braid angle of from about 120 degrees to about 150 degrees on a braid mandrel of from about 3 mm to about 30 mm diameter; removing the braid from the braid mandrel; disposing the braid on an annealing mandrel having an outer diameter of from about 0.2 mm to about 10 mm smaller than the braid mandrel diameter; annealing the braid at a temperature between about the polymer glass-transition temperature and the melting temperature for a time period between about 5 and about 120 minutes; and allowing the stent to cool.

Bioabsorbable polymer resins are commercially available. Bioabsorbable resins such as PLA, PLLA, PDLA, PGA and other bioabsorbable polymers are commercially available from several sources including PURAC America, Inc. of Lincolnshire, Ill.

Still other objects and advantages of the present invention and methods of construction of the same will become readily apparent to those skilled in the art from the following detailed description, wherein only the preferred embodiments are shown and described, simply by way of illustration of the best mode contemplated of carrying out the invention. As will be realized, the invention is capable of other and different embodiments and methods of construction, and its several details are capable of modification in various obvious respects, all without departing from the invention. Accordingly, the drawing and description are to be regarded as illustrative in nature, and not as restrictive.

DETAILED DESCRIPTION OF THE INVENTION

Figure 1:
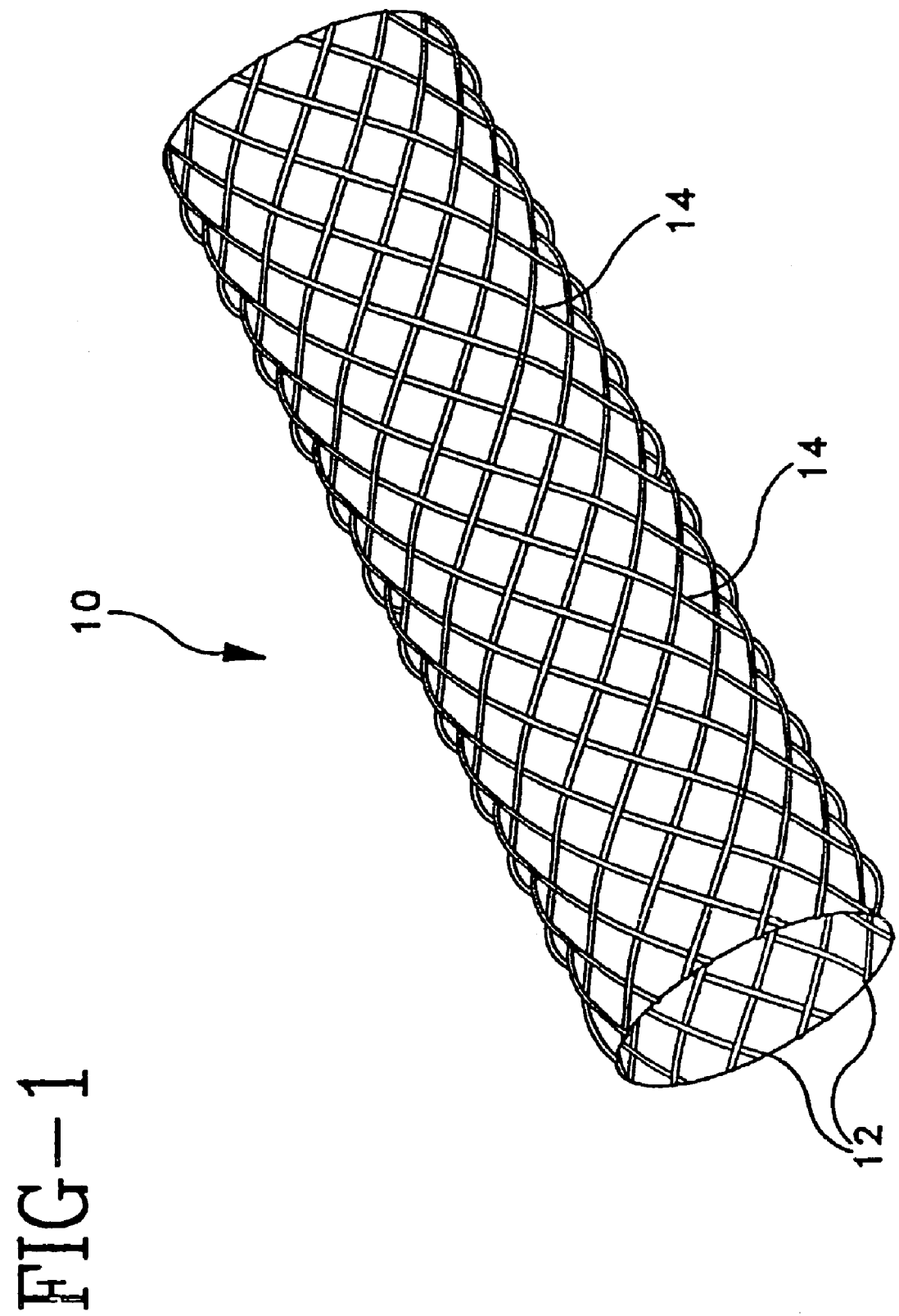
FIG. 1 is an isometric view of a stent in accordance with the present invention, illustrating the braided configuration of the filaments.
Figure 2:
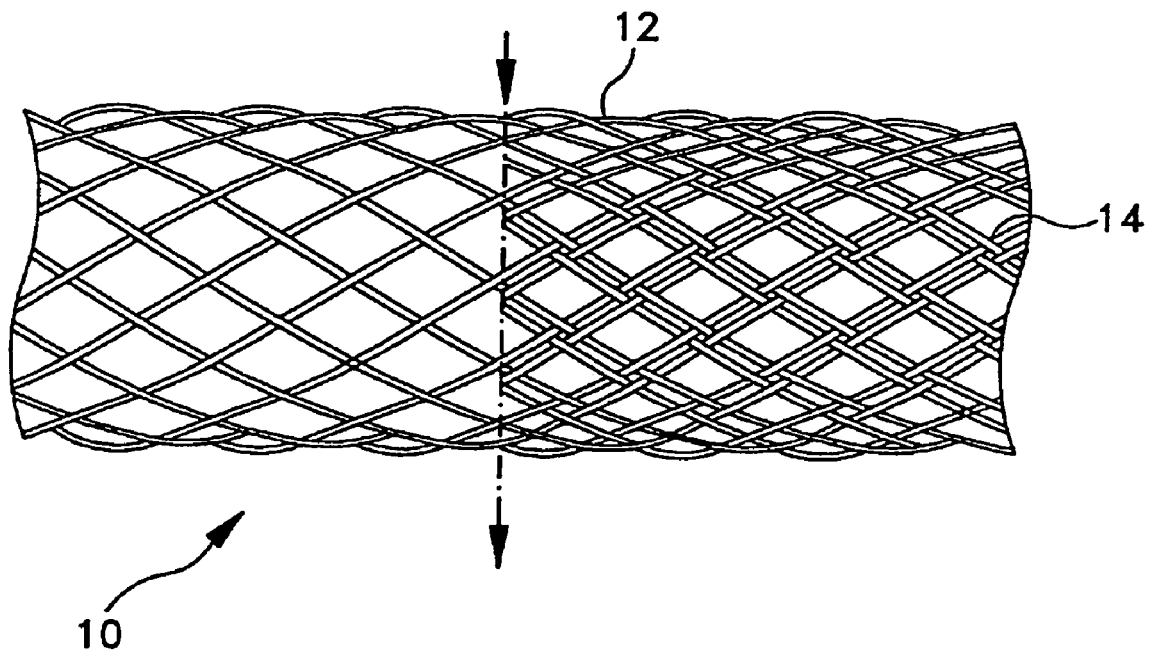
FIG. 2 is a partial longitudinal cross-sectional view of the stent shown in FIG. 1.

A bioabsorbable implantable prosthesis or stent 10 in accordance with the present invention is illustrated generally in FIGS. 1 and 2. Stent 10 is a tubular device formed from two sets of oppositely-directed, parallel, spaced-apart and helically wound elongated strands or filaments 12. The sets of filaments 12 are interwoven in an over and under braided configuration intersecting at points such as 14 to form an open mesh or weave construction. As described in greater detail below, at least one and preferably all filaments 12 consists of one or more commercially available grades of polylactide, poly-L-lactide (PLLA), poly-D-lactide (PDLA), polyglycolide (PGA), polydioxanone, polycaprolactone, polygluconate, polylactic acid-polyethylene oxide copolymers, modified cellulose, collagen, poly(hydroxybutyrate), polyanhydride, polyphosphoester; poly(amino acids), poly(alpha-hydroxy acid) or related copolymers materials. Methods for fabricating stents 10 are generally known and disclosed, for example, in the Wallsten U.S. Pat. No. 4,655,771 and the Wallsten et al. U.S. Pat. No. 5,061,275.

Stent 10 is shown in its expanded or relaxed state in FIGS. 1 and 2, i.e., in the configuration it assumes when subject to no external loads or stresses. The filaments 12 are resilient, permitting the radial compression of stent 10 into a reduced-radius, extended-length configuration or state suitable for delivery to the desired placement or treatment site through a body vessel (i.e., transluminally). Stent 10 is also self-expandable from the compressed state, and axially flexible.

Stated another way, stent 10 is a radially and axially flexible tubular body having a predetermined diameter that is variable under axial movement of the ends of the body relative to each other. The stent 10 is composed of a plurality of individually rigid but flexible and elastic thread elements or filaments 12, each of which extends in a helix configuration along a longitudinal center line of the body as a common axis. The filaments 12 define a radially self-expanding body. The body may be provided by a first number of filaments 12 having a common direction of winding but axially displaced relative to each other, and crossing a second number of filaments 12 also axially displaced relative to each other but having an opposite direction of winding.

The tubular and self-expandable body or structure formed by the interwoven filaments 12 is a primary prosthetically-functional structure of stent 10, and for this reason the device can be considered to substantially consist of this structure to the exclusion of other structures. However, it is known that other structures and features can be included in stents, and in particular features which enhance or cooperate with the tubular and self-expandable structure or which facilitate the implantation of the structure. One example is the inclusion of radiopaque markers on the structure which are used to visualize the position of the stent through fluoroscopy during implantation. Another example is the inclusion of a covering 15 or additional interwoven filaments, for instance, to reduce the porosity or open spaces in the structure so that the stent can be used to prevent tissue ingrowth or be used as a graft. Other examples include collapsing threads or other structures to facilitate repositioning and removal of the stent. Stents of these types nonetheless still substantially consist of the tubular and self-expandable structure formed by interwoven filaments 12 and shown in FIGS. 1 and 2. Furthermore, many of the desirable features and properties of stent 10 will be present if some, but not all, of the filaments 12 consist of a bioabsorbable polymeric material.

An implantable bioabsorbable stent 10 may be made by a preferred method of braiding such that 10–36 independent strands of 0.15–0.60 mm diameter bioabsorbable polymeric filament are interwoven into helical shape strands on a round bar mandrel of 3–30 mm diameter such that one-half of the number of helical strands are wound clockwise and one-half are wound counterclockwise and such that each clockwise helical strand is adjacent (interbraided) to a counterclockwise strand, the tubular braid is made with strand braid angles (angle between two filaments in the longitudinal or axial direction) of 120–150 degrees (pitch angles (angle between a filament and transverse axis of the stent) of 15–45 degrees) while on the braid bar mandrel, the braid is slid off of the braid bar and onto a 0.2–10 mm smaller diameter annealing bar or tube mandrel, each end of the braid pulled or compressed to cause axial extension or compression of the braid on the anneal mandrel, or left free, and each end of the braid secured on each end of the anneal mandrel to fix the preset axial position of the braid, or left free, annealing the braid on the anneal mandrel at a temperature between the glass-transition temperature and melting temperature of the polymer for 5–120 minutes in air, vacuum, or inert atmosphere, cooling the annealed braid on the anneal mandrel to about room temperature, sliding the braid off of the anneal mandrel and cutting it to the desired stent length. Another preferred embodiment includes at least one bioabsorbable-radiopaque marker strand.

Figure 3:
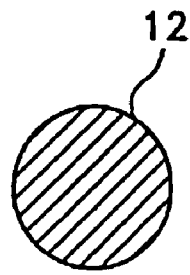
FIG. 3 is a cross-sectional view of one of the filaments of the stent shown in FIG. 1.

FIG. 3 is a cross-sectional view of one of the polymeric filaments 12. As shown, the filaments 12 are substantially homogeneous in cross section.

EXAMPLE 1

Example Four batches (53, 54, 55, 56) of PLLA monofilament 12 were produced by the supplier, Albany International Research Corporation included eight strands collected on separate spools. Four spools were randomly selected from each batch and tested by the supplier. Processing information and supplier test results are set forth below in Table 1.

TABLE 1

| Filament Spool No. | Average Diameter, mm | Diameter Standard. Deviation. | Mean Inherent Viscosity Of As Received Filament, Deciliter per gram (dl/g) | Processing History DR = Draw Ratio |
|---|---|---|---|---|
| 53-1 | .233 | .005 | 2.89 | final DR = 6 |
| 53-3 | .240 | .005 | 2.98 | final DR = 6 |
| 53-6 | .240 | .005 | 2.86 | final DR = 6 |
| 53-8 | .252 | .007 | 2.78 | final DR = 6 |
| 54-1 | .232 | .007 | 3.23 | final DR = 8 |
| 54-3 | .220 | .007 | 3.31 | final DR = 8 |
| 54-4 | .234 | .007 | 3.22 | final DR = 8 |
| 54-6 | 239 | .006 | 3.14 | final DR = 8 |
| 55-1 | 236 | .007 | 3.29 | DR of 8 and mill anneal |
| 55-3 | .227 | .008 | 3.32 | DR of 8 and mill anneal |
| 55-4 | .248 | .007 | 3.28 | DR of 8 and mill anneal |
| 55-6 | .241 | .006 | 3.20 | DR of 8 and mill anneal |
| 56-1 | .237 | .016 | 2.86 | final DR of 8 and high extrusion temp. |
| 56-4 | .247 | .009 | 2.82 | final DR of 8 and high extrusion temp. |
| 56-5 | .243 | .011 | 2.83 | final DR of 8 and high extrusion temp. |
| 56-6 | .246 | .009 | 2.86 | final DR of 8 and high extrusion temp. |

One spool from each batch was randomly selected for further testing. The PLLA filaments produced in spools 53-8, 54-6, 55-6, and 56-6 were tested for their mechanical properties in the condition received from the supplier and again tested in an annealed condition. Testing included measurement of the filament diameter, tensile testing, and rotating beam-type fatigue testing. Measurements of mean filament properties in an as-received condition are summarized in Table 2 and measurements of mean filament properties after annealing at 140° C. for 15 minutes are summarized in Table 3.

TABLE 2

| Spool # | Diameter, mm | Ultimate Tensile Strength (UTS), MPa | 0.2°/a offset Yield Strength (YS), MPa | % Elongation at break | Modulus, MPa |
|---|---|---|---|---|---|
| 53-8 | .251 | 384 | 162 | 23.5 | 7102 |
| 54-6 | .231 | 628 | 203 | 22.6 | 8826 |
| 55-6 | .226 | 676 | 190 | 27.6 | 7447 |
| 56-6 | .221 | 659 | 191 | 31.7 | 6550 |

TABLE 3

| Spool # | Diameter, mm | Ultimate Tensile Strength (UTS), MPa | 0.2% Offset Yield Strength (YS), MPa | % Elongation at break | Modulus, MPa |
|---|---|---|---|---|---|
| 53-8 | .236 | 655 | 141 | 37.3 | 3448 |
| 54-6 | .231 | 605 | 181 | 29.4 | 6826 |
| 55-6 | .229 | 642 | 181 | 30.2 | 6619 |
| 56-6 | .236 | 615 | 172 | 34.0 | 5378 |

Experimentation shows that the diameters of the strands did not change substantially after annealing. The tensile breaking loads were lowest for batch #53 which was drawn at the lowest drawing ratio of 6. The break loads for all four batches ranged from about 4 to 6 lbs. (18 to 28 N) before annealing and the break loads were about the same range after annealing. The mean breaking load was highest for batch #55 which was mill annealed after the final draw ratio of 8. However, after annealing, the difference in mean break loads in the three batches extruded with a draw ratio of 8 was not significant. The mean tensile elongation was highest for batch #56 which was extruded at a higher temperature. The tensile modulus values (Young's modulus) were about one million psi (8000 Mpa) prior to annealing and the tensile modulus values were slightly reduced after annealing, with the exception of batch #53 (DR=6) where the tensile modulus was nearly reduced in half. There were no significant changes in strength or modulus as a result of the annealing at 140° C. for 15 minutes. The annealing was performed to relax and homogenize the material after braiding and to allow the braid to shrink to the desired annealed stent diameter.

Rotating beam bending fatigue testing was performed on annealed specimens from each of the four batches. Testing of the as-extruded filaments was unsuccessful because the filaments did not appear stiff enough to be capable of withstanding torsional loading. However, testing was performed using the Valley Instruments U-bend wire spin fatigue machines. One end of the test specimen was gripped by a chuck, the specimen was formed into an arc, and the free end was inserted into a stationary holder to maintain the arc. The arc dimensions and material modulus were used to calculate the maximum bending stress at the apex of the arc. The specimen was then rotated at 3600 rpm and the surface of the test specimen is cycled between compressive and tensile bending stresses at the apex of the arc. The number of cycles to failure (complete fracture, kinking, or longitudinal splitting) was recorded for each test, and the results are plotted in a stress vs. cycles to failure plot (S/N fatigue plots in FIGS. 15–18).

Batch #53, with the lowest draw ratio of 6, had lower fatigue results or failures at lower stresses than the batches extruded at the higher draw ratio of 8. Batches #54 and #55 had similar fatigue results, and batch #56 had lower results than #54 and #55, but had higher results than 53. The results indicate that the higher draw ratio and lower extrusion temperatures are preferred if fatigue strength is to be maximized.

EXAMPLE 2–10

A stent 10 was fabricated from about 0.24 mm diameter PLLA monofilament 12 from spool 55-6. This spool was selected because it had high UTS and modulus which are desirable mechanical properties for obtaining high stent radial strength. The stent 10 was braided onto a 10 mm diameter steel bar mandrel. The braid was constructed of 24 strands and the braid angle was 130 degrees (pitch angle of 25 degrees). The included angle between interbraided filaments in the axial orientation is termed "braid angle" prior to annealing and is termed "filament crossing angle" after annealing. A braid becomes a stent after annealing.

Braid annealing was performed to relax the stresses in the filaments resulting from braiding and to set the stent shape. Three anneal trials were performed. In the first trial, the braid was slid onto a 10 mm diameter tubular mandrel. In this trial, the braid was difficult to put on the mandrel because the braid inside diameter was very close to the mandrel diameter. In the second trial, the braid was easily put onto a 9 mm diameter mandrel. The braid was compressed axially and held in this state with plastic tie-wraps. The third trial was performed in the same manner as the second trial.

After annealing, the braid had shrunk down onto the anneal mandrel and the annealed filament crossing angle was higher than the original braid angle. The annealed uncut stents were measured with a laser micrometer for external diameter. A scale was used to measure pitch length. The results are presented in the following Table 4.

TABLE 4

| Dimension | Trial #1 | Trial #2 | Trial #3 |
|---|---|---|---|
| Average External Diameter, mm | 10.65 | 9.83 | 9.87 |
| Pitch Length, mm | 10.34 | 10.34 | 10.08 |
| Calculated Filament Crossing Angle, ° | 145 | 143 | 144 |

The average external diameter is the average value of the external stent diameters measured. The pitch length is the length of one complete filament helix. The filament crossing angle was calculated from the average external diameter and the pitch length using the equation, angle=$180°-2\tan^{-1}(P/\pi D)$, where p is the pitch length and D is the average external stent diameter minus twice the filament diameter.

The uncut stents 10 were then cut to 30 mm lengths at the free diameter and were loaded onto 10 French catheter delivery systems. The delivery system is constructed of an inner tube which slides over the guidewire in an angioplasty procedure and an outer tube. The stent is axially extended and radially contracted onto the outer surface of the inner tube and the outer tube is slid coaxially over the constrained stent to hold it in the constrained condition. When the delivery system is positioned in the stricture to be treated, the outer tube is pulled back allowing the stent to spring off of the inner tube and self-expand to brace open the stricture. The nominal outer tube inner diameter was 2.8448 mm and the inner tube outer diameter was 1.3208 mm. The calculated gap between the inner and outer tube was 0.7642 mm. The stents 10 were left on the delivery systems for 30 minutes and were then were deployed onto the benchtop.

Dimensions of the nine 10 mm PLLA stents 10 before loading and after deployment are listed in Table 5.

TABLE 5

| Trial # | Initial Length, mm | Deployed Length, mm | Initial Diameter, mm | Deployed Diameter, mm | Self-expansion (deployed/ initial Ø) |
|---|---|---|---|---|---|
| 1a | 32 | 90 | 10.69 | 6.2 | 0.58 |
| 1b | 30 | 88 | 10.73 | 6.6 | 0.62 |
| 1c | 30 | 90 | 10.63 | 6.2 | 0.58 |
| 2a | 30 | 80 | 9.94 | 5.2 | 0.52 |
| 2b | 30 | 68 | 9.83 | 6.2 | 0.63 |
| 2c | 30 | 80 | 9.88 | 6.4 | 0.65 |
| 3a | 30 | 80 | 9.96 | 5.0 | 0.50 |
| 3b | 30 | 80 | 9.76 | 5.7 | 0.58 |
| 3c | 30 | 80 | 9.80 | 5.6 | 0.57 |

Initial length and diameter were measured on the cut stent in its free state on the table after annealing but before being loaded for deployment. Deployed length and diameter were measured after the annealed stent was loaded on the 10 French delivery system and deployed on the table and allowed to reach its free state. The lengths of stents upon implantation will be longer upon implantation because the stent will only reach about 80% of the deployed diameter when implanted.

The stent dimensional changes resulting from loading appeared consistent from test specimen to test specimen. The stents 10 were deformed by the constraint on the delivery system. This consistency allows the dimensional changes to be anticipated and accounted for during design. The dimensions of deployed stents 10 were considerably changed relative to the dimensions of the same stents 10 prior to loading. The deformation was not permanent and the stents 10 reverted toward the original dimensions over a period of days after deployment. For instance, the stents 10 from trial #1 opened up to almost 90% of their original pre-loaded diameter after about 3 days from the deployment time.

Residual stresses appear to remain in the material from delivery system constraint and are relieved at room temperature over a period of time which allows stent 10 to return toward its original undeformed condition. If the residual stresses can be minimized, or if the magnitude of the residual stresses relative to the yield strength can be minimized, or if stress relief can be accelerated to seconds instead of days, it may be possible to increase the amount of self-expansion immediately upon deployment. In order to avoid imparting significant residual stresses, loading is preferably performed with less stressing of the stent 10, i.e., use of a larger profile delivery system, use of a larger gap between inner and outer tubes, a gentle loading technique, or use of an alternate delivery system design.

Figure 11:
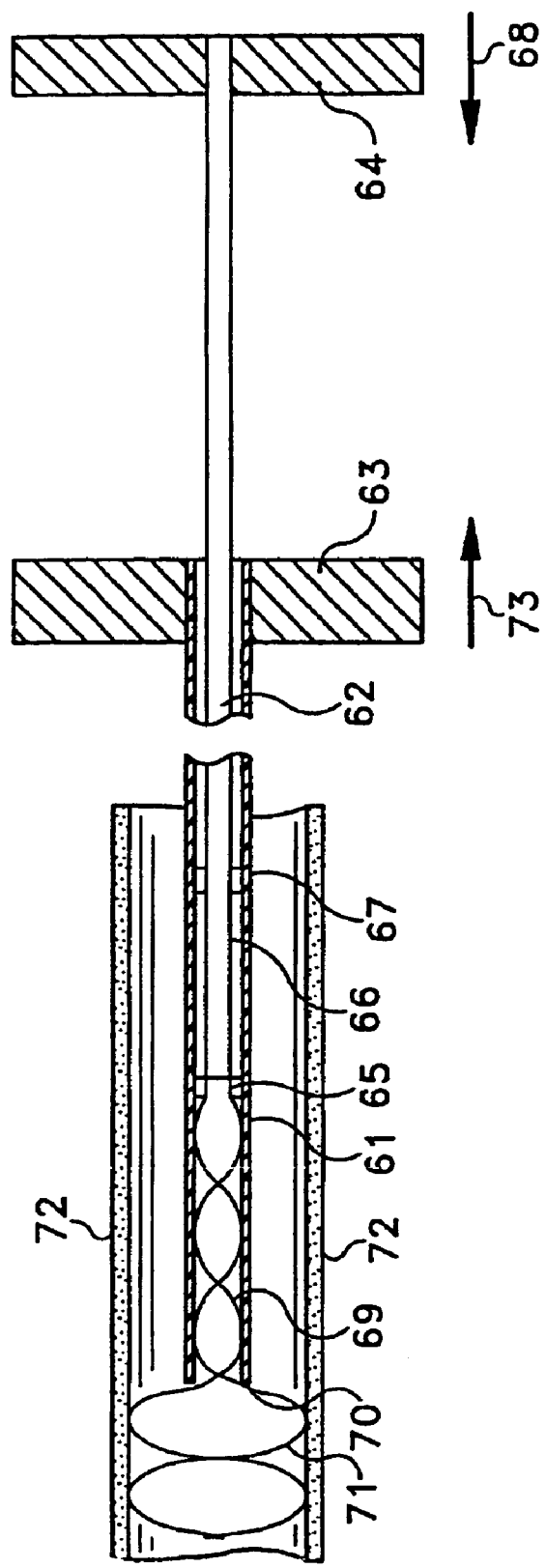
FIG. 11 is a side view of a pusher-type delivery device.

The use of a pusher-type delivery system results in greater self-expansion of the stent than a coaxial inner-outer tube-type delivery system as shown in FIG. 11. Reference is made to U.S. Pat. No. 4,954,126. For example, pushing the proximal end of the stent out the distal end of the delivery system results in more self expansion than when the stent is released by sliding back the outer tube of the catheter delivery system because the stent 10 is under axial compression during deployment.

EXAMPLE 11–15

Experiments were performed using various PLLA monofilament braided stents 10. The stents 10 were annealed on various sized tubular anneal mandrels and then loaded and deployed from delivery systems. The 36 French delivery systems pushed the stent 10 out of a stainless steel outer tube. The 10 and 18 French delivery systems were inner and outer tube catheter type systems where the outer tube is pulled back to allow the stent to spring open. The external diameter of the stents 10 were measured after annealing and after deployment from the delivery system. Radial force testing was performed on deployed stents 10 by wrapping a metal wire around the stent circumference at the center of the stent length and pulling on each end of the wire to cause radial contraction of the stent diameter to one-half of its original (free) value. The ends of the wire were attached to a load cell to measure the force necessary to cause radial contraction.

The braid mandrel diameter is the external diameter of the braid bar. The delivery system size is the external diameter in French size (or about three times the diameter in mm). Deployed stent external diameter and radial force were measured on stents released from the delivery system onto the table. Percent self-expansion is (deployed diameter/ annealed diameter)×100.

The experimental results for PLLA braided stent load and deployment trials and radial force testing are shown in Table 6 below. The inner/outer tube catheter type of delivery system yielded lower percent self-expansion than the pusher type of delivery system (58–76% vs. 85–93%, respectively).

TABLE 6

| # of Filaments In Braid | Filament Diameter, Mm | Braid Mandrel Dia., Mm | Anneal Mandrel Dia., Mm | Annealed Stent External Dia., Mm. | Delivery System Size, French | Deployed Stent External Dia., Mm | Percent Self- Expansion | Radial Force At Half-Stent Dia., Grams |
|---|---|---|---|---|---|---|---|---|
| 24 | .25 | 10.0 | 9.0 | 9.9 | 10 | 5.7 | 58 | 64 |
| 30 | .35 | 18.5 | 18.0 | 19.1 | 18 | 14.5 | 76 | 90 |
| 36 | .36 | 25.8 | 18.0 | 19.4 | 36 | 16.4 | 85 | 200 |
| 36 | .36 | 25.8 | 22.0 | 23.3 | 36 | 19.7 | 85 | 132 |
| 36 | .36 | 25.8 | 24.0 | 25.2 | 36 | 23.4 | 93 | 113 |

Experimentation has shown that there is a nearly linear relationship between stent radial force and annealed stent diameter for a given braid design and delivery system design. The present invention provides a method to determine the preferred anneal mandrel size for a particular polymeric stent 10 design. For example, if a PLLA braided filament stent 10 is desired to have a radial force equal to a particular metal stent or polymer stent, the radial force of the benchmark stent can be measured and used as the target value. Further, a stent 10 of a size at or about the desired implant size from Table 7 above would then be annealed on two different sizes of anneal mandrels and the radial force of the deployed annealed stents would be measured. The slope and intercept values would be calculated from the test results. The linear equation can then be used to solve for the annealed stent diameter which will yield the target radial force value. Example 16 below illustrates the methodology.

EXAMPLE 16

Figure 13:
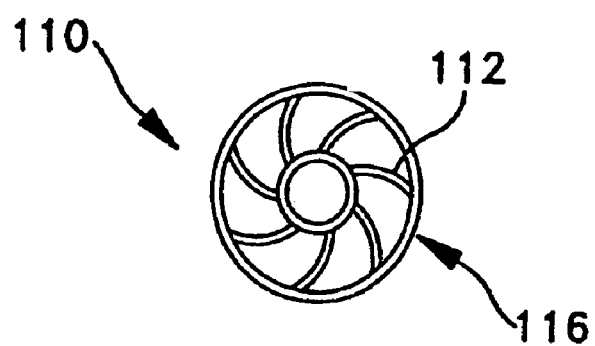
FIG. 13 is an end view of the stent shown in FIG. 14.
Figure 14:
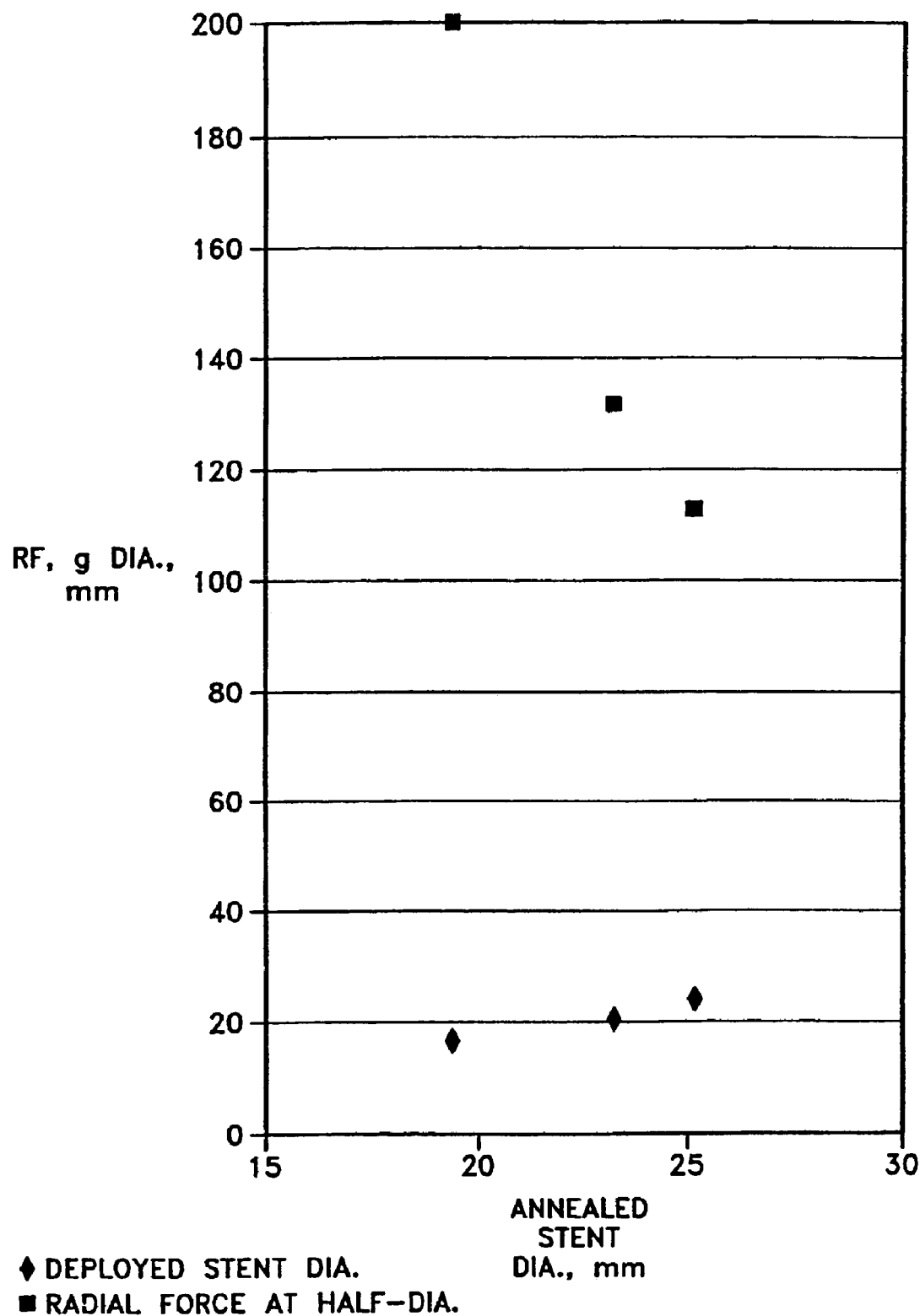
FIG. 14 is a plot illustrating PLLA stent radial force and deployed diameter vs. annealed stent diameter.
Figure 15:
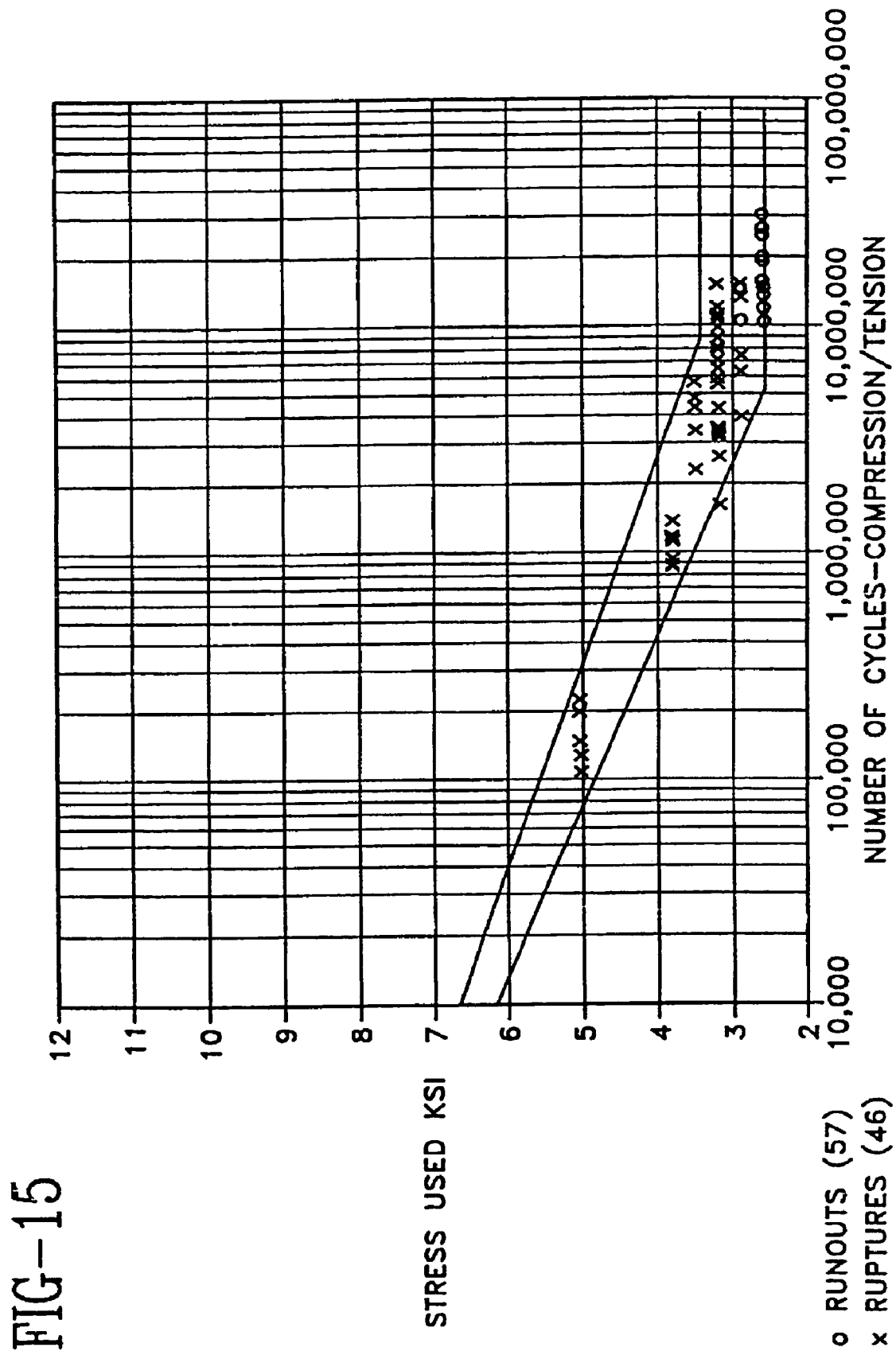
FIGS. 15–18 are graphs of fatigue test results of PLLA filament batches.
Figure 16:
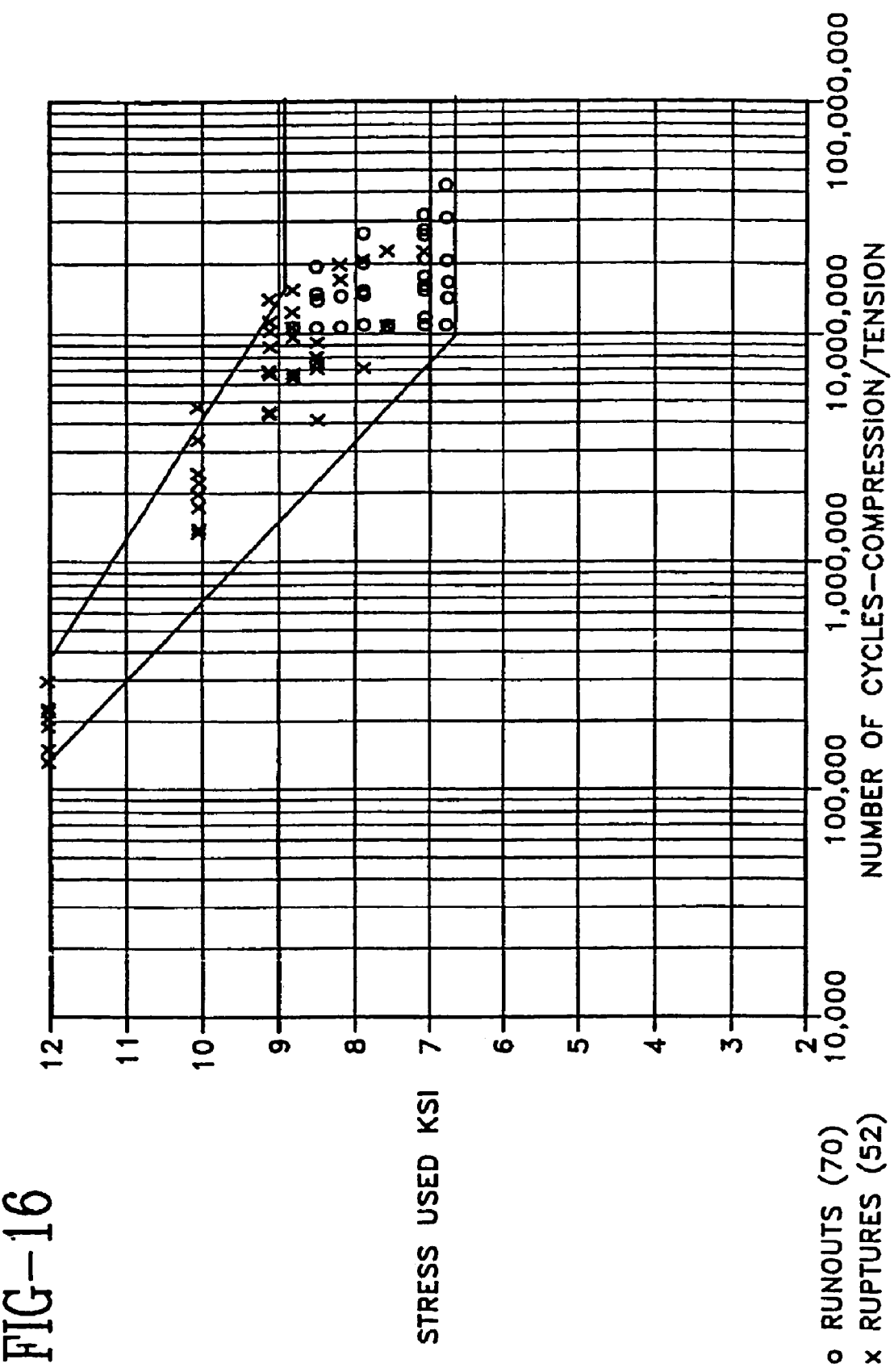
Figure 17:
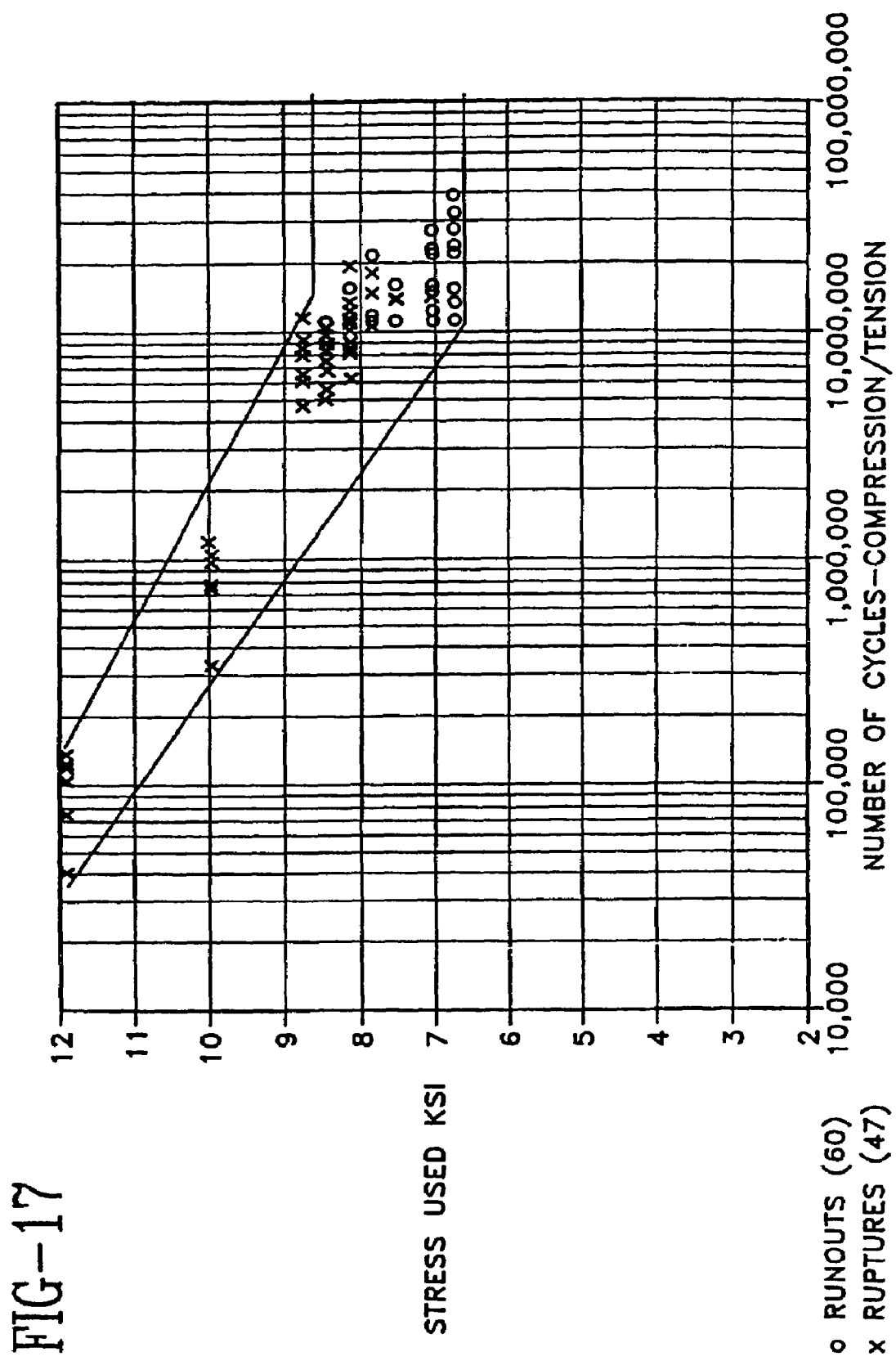
Figure 18:
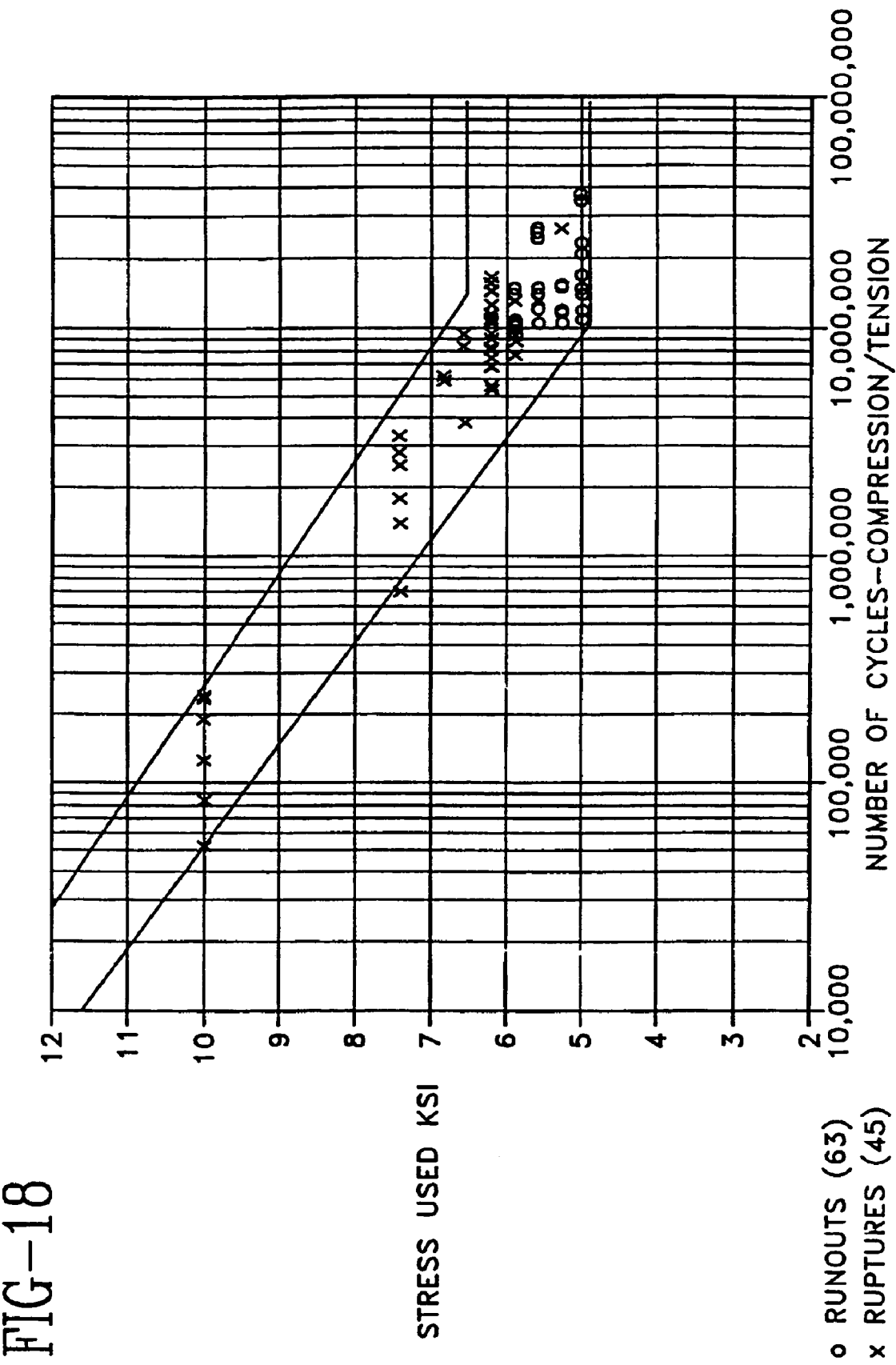

The radial force data in Table 6 for the 36-filament stents was plotted against the values for annealed stent diameter and is illustrated in FIG. 13 for stents 10 with 36 strands of 0.36 mm diameter PLLA filament annealed at 140° C. for 15 minutes and deployed from a 36 French pusher-type delivery system.

The graph is nearly linear. The slope and intercept were calculated using two sets of coordinates from the line (200 g, 19.4 mm and 113 g, 25.2 mm).

$RF(g)=m(\text{ann } \emptyset)+b$ where $m$ is the slope and $b$ is the intercept.

$m=200-113/19.4-25.2=-15$ $200=(-15)(19.4)+b \quad b=491$ $RF(g)=(-15)(\text{ann } \emptyset)+491$      Equation 1 (36-filament PLLA scent)

For example, if the target value for radial force is 150 g:

$150=(-15)(\text{ann } \emptyset)+491$ annealed stent diameter=22.73 mm
anneal mandrel diameter=stent diameter−4 d where d is the filament diameter
anneal mandrel diameter=21.29 mm Accordingly, it is possible to manufacture a bioabsorbable stent which is predicted to yield a desired radial force after deployment from the delivery system. For example, from Table 6 or 7, a stent 10 design of 36 strands has a 0.36 mm diameter PLLA filament. The stent 10 can be then annealed on a 21.29 mm diameter tubular mandrel. The annealed stent 10 can be loaded onto a 36 French pusher delivery system for implantation.

Similar experimentation was used to predict the deployed stent diameter (implant size) from the annealed stent diameter for a given braid design and delivery system size. A graph of the deployed stent diameter vs. annealed stent diameter is nearly linear, so a linear equation is used to predict the deployed stent diameter. Two stents 10 were made from two different anneal mandrel sizes and then loaded and deployed from the delivery system. The linear equation can be determined from the experimental results. Subsequently, the linear equation is used to predict the anneal mandrel size necessary to yield a target implant size.

EXAMPLE 17

The deployed stent diameter data in Table 6 for the 36-filament stents was plotted against the values for annealed stent diameter (FIG. 13). The graph is nearly linear. The slope and intercept were calculated using two sets of coordinates from the line (16.4 mm, 19.4 mm and 23.4 mm, 25.2 mm).

deployed $\emptyset=m(\text{ann } \emptyset)+b$ where $m$ is the slope and $b$ is the intercept.

$m=16.4-23.4/19.4-25.2=1.21$ $16.4=(1.21)(19.4)+b \quad b=7.07$ deployed $\emptyset=(1.21)(\text{ann } \emptyset)-7.0$ Equation 2 (36-filament PLLA stent)

For example, if the target value for deployed diameter is 20 mm:

$20=(1.21)(\text{ann } \emptyset)-7.07$ annealed stent diameter=22.37 mm
anneal mandrel diameter=stent diameter−4 d where d is the filament diameter
anneal mandrel diameter=20.93 mm Accordingly, the present invention provides a bioabsorbable stent which provides a desired radial force and diameter after deployment from the delivery system. For example, from Table 6 or 7, a stent 10 design of 36 strands has a 0.36 mm diameter PLLA filament. The stent 10 can be annealed on a 20.93 mm diameter tubular mandrel and loaded onto a 36 French pusher delivery system for implantation. Furthermore, the stent 10 would yields a radial force of about 155 grams as previously shown.

Using linear equations to predict the annealed stent diameter and radial force minimizes the total number of design iterations for manufacturing and testing. Only two designs must be made to allow the predictive equations to be developed.

The PLLA filament stent 10 from Table 7 may be used with the required delivery system. The linear equations can be derived using the two test series, and thereafter the stent design may be optimized with regard to radial force and implant size by predicting the necessary anneal mandrel size.

TABLE 7

| # of filament strands in stent | braid mandrel diameter, mm | braid angle, degrees | PLLA diameter, mm | PDLA diameter, mm | PLLA/PDLA diameter, mm | PGA diameter, mm |
| --- | --- | --- | --- | --- | --- | --- |
| 10 | 3–6 | 120–150 | .15–.25 | .15–.25 | .15–.25 | .20–.30 |
| 10 | 3–6 | 120–150 | .20–.30 | .20–.30 | .20–.30 | .25–.35 |
| 12 | 3–8 | 120–150 | .20–.30 | .20–.30 | 20–.30 | .25–.35 |
| 12 | 3–8 | 120–150 | .35–.45 | .35–.45 | .35–.45 | .40–:50 |
| 15 | 6–10 | 120–150 | .30–.40 | .30–.40 | .30–.40 | .35–.45 |
| 15 | 6–10 | 120–150 | .35–.45 | .35–.45 | .35–.45 | .40–.50 |

TABLE 7-continued

| # of filament strands in braid | braid mandrel diameter, mm | braid angle, degrees | PGA/PLLA diameter, mm | PGA/ polycaprolactone diameter, mm | Polydioxanone diameter, mm | PGA/ trimethylene carbonate diameter, mm |
|---|---|---|---|---|---|---|
| 18 | 7–12 | 120–150 | .35–.45 | .35–.45 | .35–.45 | .40–.50 |
| 18 | 7–12 | 120–150 | .40–.50 | .40–.50 | .40–.50 | .45–.55 |
| 20 | 3–9 | 120–150 | .20–.30 | .20–.30 | .20–.30 | .25–.35 |
| 24 | 8–12 | 120–150 | .20–.30 | .20–.30 | .20–.30 | .25–.35 |
| 24 | 9–14 | 120–150 | .25–.35 | .25–.35 | .25–.35 | .30–.40 |
| 24 | 12–18 | 120–150 | .30–.40 | .30–.40 | .30–.40 | .35–.45 |
| 30 | 16–26 | 120–150 | .30–.40 | .30–.40 | .30–.40 | .35–.45 |
| 36 | 20–30 | 120–150 | .35–.45 | .35–.45 | .35–.45 | .40–.50 |
| 24 | 14–20 | 120–150 | .35–.45 | .35–.45 | .35–.45 | .40–.50 |

| # of filament strands in braid | braid mandrel diameter, mm | braid angle, degrees | PGA/PLLA diameter, mm | PGA/ polycaprolactone diameter, mm | Polydioxanone diameter, mm | PGA/ trimethylene carbonate diameter, mm |
|---|---|---|---|---|---|---|
| 10 | 3–6 | 120–150 | .20–.30 | .22–.32 | 25–.35 | .22–.32 |
| 10 | 3–6 | 120–150 | .25–.35 | .27–.37 | .30–.40 | .27–.37 |
| 12 | 3–8 | 120–150 | .25–.35 | .27–.37 | .30–.40 | .27–.37 |
| 12 | 3–8 | 120–150 | .40–.50 | .42–.52 | .45–.55 | .42–.52 |
| 15 | 6–10 | 120–150 | .35–.45 | .37–.47 | .40–.50 | .37–.47 |
| 15 | 6–10 | 120–150 | .40–.50 | .42–.52 | .45–.55 | .42–.52 |
| 18 | 7–12 | 120–150 | .40–.50 | .42–.52 | .45–.55 | .42–.52 |
| 18 | 7–12 | 120–150 | .45–.55 | .47–.57 | .50–.60 | .47–.57 |
| 20 | 3–9 | 120–150 | .25–.35 | .27–.37 | .30–.40 | .27–.37 |
| 24 | 8–12 | 120–150 | .25–.35 | .27–.37 | .30–.40 | .27–.37 |
| 24 | 9–14 | 120–150 | .30–.40 | .32–.42 | .35–.45 | .32–.42 |
| 24 | 12–18 | 120–150 | .35–.45 | .37–.47 | .40–.50 | .37–.47 |
| 30 | 16–26 | 120–150 | .35–.45 | .37–.47 | .40–.50 | .37–.47 |
| 36 | 20–30 | 120–150 | .40–.50 | .42–.52 | .45–.55 | .42–.52 |
| 24 | 14–20 | 120–150 | .40–.50 | .42–.52 | .45–.55 | .42–.52 |

The experiments indicate that stents 10 fabricated from the PLLA filament have desirable characteristics for certain applications. The stents 10 have measurable resistance to compression and exert a more gentle force (less radial force) than the Elgiloy® stent on the lumen wall. Stents 10 are therefore durable and flexible, and capable of being moved through curved vessels or lumens during delivery. The PLLA material is highly biocompatible.

Although PLLA is the most preferred absorbable polymer, other polymers can also be used. In particular, poly-D-lactide (PDLA), polyglycolide (PGA), polydioxanone, polycaprolactone, polygluconate, polylactic acid-polyethylene oxide copolymers, modified cellulose, collagen, poly(hydroxybutyrate), polyanhydride, polyphosphoester, poly (amino acids), or related copolymers materials will offer advantages similar to the most preferred polymer.

EXAMPLE 18

Stents 110 can be fabricated from 10 filament strands of 0.15–0.25 mm diameter PLLA, PDLA, PLLA-PDLA copolymer, 0.20–0.30 mm diameter PGA, PGA-PLLA copolymer, 0.22–0.32 mm diameter PGA-polycaprolactone copolymer, PGA-trimethylcarbonate copolymer, or 0.25–0.35 mm diameter polydioxanone on a 3–6 mm diameter braid mandrel with a filament braid angle of 120–150 degrees while the braid is on the braid mandrel and annealed on a bar or tube mandrel that has an outer diameter 0.2–10 mm smaller than the braid mandrel diameter at a temperature between the polymer glass-transition temperature and the melting temperature for 5–120 minutes in air, vacuum, or inert atmosphere, with the braid in an axially extended, free, or contracted position, cooled to about room temperature, slid off the anneal mandrel, cut to the desired stent length, and loaded onto a delivery system at least 5 French in size.

EXAMPLE 19

Stents 10 can be fabricated from 10 filament strands of 0.20–0.30 mm diameter PLLA, PDLA, PLLA-PDLA copolymer, 0.25–0.35 mm diameter PGA, PGA-PLLA copolymer, 0.27–0.37 mm diameter PGA-polycaprolactone copolymer, PGA-trimethylcarbonate copolymer, or 0.30–0.40 mm diameter polydioxanone on a 3–6 mm diameter braid mandrel with a filament braid angle of 120–150 degrees while the braid is on the braid mandrel and annealed on a bar or tube mandrel that has an outer diameter 0.2–10 mm smaller than the braid mandrel diameter at a temperature between the polymer glass-transition temperature and the melting temperature for 5–120 minutes in air, vacuum, or inert atmosphere with the braid in an axially extended, free, or contracted position, cooled to about room temperature, slid off the anneal mandrel, cut to the desired stent length, and loaded onto a delivery system at least 7 French in size.

EXAMPLE 20

Stents 10 can be fabricated from 12 filament strands of 0.20–0.30 mm diameter PLLA, PDLA, PLLA-PDLA copolymer, 0.25–0.35 mm diameter PGA, PGA-PLLA copolymer, 0.27–0.37 mm diameter PGA-polycaprolactone copolymer, PGA-trimethylcarbonate copolymer, or 0.30–0.40 mm diameter polydioxanone on a 3–8 mm diameter braid mandrel with a filament braid angle of 120–150 degrees while the braid is on the braid mandrel and annealed on a bar or tube mandrel that has an outer diameter 0.2–10 mm smaller than the braid mandrel diameter at a temperature between the polymer glass-transition temperature and the melting temperature for 5–120 minutes in air, vacuum, or inert atmosphere with the braid in an axially extended, free, or contracted position, cooled to about room temperature, slid off the anneal mandrel, cut to the desired stent length, and loaded onto a delivery system at least 7 French in size.

EXAMPLE 21

Stents 10 can be fabricated from 12 filament strands of 0.35–0.45 mm diameter PLLA, PDLA, PLLA-PDLA copolymer, 0.40–0.50 mm diameter PGA, PGA-PLLA copolymer, 0.42–0.52 mm diameter PGA-polycaprolactone copolymer, PGA-trimethylcarbonate copolymer, or 0.45–0.55 mm diameter polydioxanone on a 3–8 mm diameter braid mandrel with a filament braid angle of 120–150 degrees while the braid is on the braid mandrel and annealed on a bar or tube mandrel that has an outer diameter 0.2–10 mm smaller than the braid mandrel diameter at a temperature between the polymer glass-transition temperature and the melting temperature for 5–120 minutes in air, vacuum, or inert atmosphere with the braid in an axially extended, free, or contracted position, cooled to about room temperature, slid off the anneal mandrel, cut to the desired stent length, and loaded onto a delivery system at least 10 French in size.

EXAMPLE 22

Stents 10 can be fabricated from 15 filament strands of 0.30–0.40 mm diameter PLLA, PDLA, PLLA-PDLA copolymer, 0.35–0.45 mm diameter PGA, PGA-PLLA copolymer, 0.37–0.47 mm diameter PGA-polycaprolactone copolymer, PGA-trimethylcarbonate copolymer, or 0.40–0.50 mm diameter polydioxanone on a 6–10 mm diameter braid mandrel with a filament braid angle of 120–150 degrees while the braid is on the braid mandrel and annealed on a bar or tube mandrel that has an outer diameter 0.2–10 min smaller than the braid mandrel diameter at a temperature between the polymer glass-transition temperature and the melting temperature for 5–120 minutes in air, vacuum, or inert atmosphere with the braid in an axially extended, free, or contracted position, cooled to about room temperature, slid off the anneal mandrel, cut to the desired stent length, and loaded onto a delivery system at least 8 French in size.

EXAMPLE 23

Stents 10 can be fabricated from 15 filament strands of 0.35–0.45 mm diameter PLLA, PDLA, PLLA-PDLA copolymer, 0.40–0.50 mm diameter PGA, PGA-PLLA copolymer, 0.42–0.52 mm diameter PGA-polycaprolactone copolymer, PGA-trimethylcarbonate copolymer, or 0.45–0.55 mm diameter polydioxanone on a 6–10 mm diameter braid mandrel with a filament braid angle of 120–150 degrees while the braid is on the braid mandrel and annealed on a bar or tube mandrel that has an outer diameter 0.2–10 mm smaller than the braid mandrel diameter at a temperature between the polymer glass-transition temperature and the melting temperature for 5–120 minutes in air, vacuum; or inert atmosphere with the braid in an axially extended, free, or contracted position, cooled to about room temperature, slid off the anneal mandrel, cut to the desired stent length, and loaded onto a delivery system at least 10 French in size.

EXAMPLE 24

Stents 10 can be fabricated from 18 filament strands of 0.35–0.45 mm diameter PLLA, PDLA, PLLA-PDLA copolymer, 0.40–0.50 mm diameter PGA, PGA-PLLA copolymer, 0.42–0.52 mm diameter PGA-polycaprolactone copolymer, PGA-trimethylcarbonate copolymer, or 0.45–0.55 mm diameter polydioxanone on a 7–12 mm diameter braid mandrel with a filament braid angle of 120–150 degrees while the braid is on the braid mandrel and annealed on a bar or tube mandrel that has an outer diameter 0.2–10 mm smaller than the braid mandrel diameter at a temperature between the polymer glass-transition temperature and the melting temperature for 5–120 minutes in air, vacuum, or inert atmosphere with the braid in an axially extended, free, or contracted position, cooled to about room temperature, slid off the anneal mandrel, cut to the desired stent length, and loaded onto a delivery system at least 10 French in size.

EXAMPLE 25

Stents 10 can be fabricated from 18 filament strands of 0.40–0.50 mm diameter PLLA, PDLA, PLLA-PDLA copolymer, 0.45–0.55 mm diameter PGA, PGA-PLLA copolymer, 0.47–0.57 mm diameter PGA-polycaprolactone copolymer, PGA-trimethylcarbonate copolymer, or 0.50–0.60 mm diameter polydioxanone on a 7–12 mm diameter braid mandrel with a filament braid angle of 120–150 degrees while the braid is on the braid mandrel and annealed on a bar or tube mandrel that has an outer diameter 0.2–10 mm smaller than the braid mandrel diameter at a temperature between the polymer glass-transition temperature and the melting temperature for 5–120 minutes, in air, vacuum, or inert atmosphere with the braid in an axially extended, free, or contracted position, cooled to about room temperature, slid off the anneal mandrel, cut to the desired stent length, and loaded onto a delivery system at least 12 French in size.

EXAMPLE 26

Stents 10 can be fabricated from 20 filament strands of 0.20–0.30 mm diameter PLLA, PDLA, PLLA-PDLA copolymer, 0.25–0.35 mm diameter PGA, PGA-PLLA copolymer, 0.27–0.37 mm diameter PGA-polycaprolactone copolymer, PGA-trimethylcarbonate copolymer, or 0.30–0.40 mm diameter polydioxanone on a 3–9 mm diameter braid mandrel with a filament braid angle of 120–150 degrees while the braid is on the braid mandrel and annealed on a bar or tube mandrel that has an outer diameter 0.2–10 mm smaller than the braid mandrel diameter at a temperature between the polymer glass-transition temperature and the melting temperature for 5–120 minutes in air, vacuum, or inert atmosphere with the braid in an axially extended, free, or contracted position, cooled to about room temperature, slid off the anneal mandrel, cut to the desired stent length, and loaded onto a delivery system at least 9 French in size.

EXAMPLE 27

Stents 10 can be fabricated from 24 filament strands of 0.20–0.30 mm diameter PLLA, PDLA, PLLA-PDLA copolymer, 0.25–0.35 mm diameter PGA, PGA-PLLA copolymer, 0.27–0.37 mm diameter PGA-polycaprolactone copolymer, PGA-trimethylcarbonate copolymer, or 0.30–0.40 mm diameter polydioxanone on a 8–12 mm diameter braid mandrel with a filament braid angle of 120–150 degrees while the braid is on the braid mandrel and annealed on a bar or tube mandrel that has an outer diameter 0.2–10 min smaller than the braid mandrel diameter at a temperature between the polymer glass-transition temperature and the melting temperature for 5–120 minutes in air, vacuum, or inert atmosphere with the braid in an axially extended, free, or contracted position, cooled to about room temperature, slid off the anneal mandrel, cut to the desired stent length, and loaded onto a delivery system at least 10 French in size.

EXAMPLE 28

Stents 10 can be fabricated from 24 filament strands of 0.25–0.35 mm diameter PLLA, PDLA, PLLA-PDLA copolymer, 0.30–0.40 mm diameter PGA, PGA-PLLA copolymer, 0.32–0.42 mm diameter PGA-polycaprolactone copolymer, PGA-trimethylcarbonate copolymer, or 0.35–0.45 mm diameter polydioxanone on a 9–14 mm diameter braid mandrel with a filament braid angle of 120–150 degrees while the braid is on the braid mandrel and annealed on a bar or tube mandrel that has an outer diameter 0.2–10 mm smaller than the braid mandrel diameter at a temperature between the polymer glass-transition temperature and the melting temperature for 5–120 minutes in air, vacuum, or inert atmosphere with the braid in an axially extended, free, or contracted position, cooled to about room temperature, slid off the anneal mandrel, cut to the desired stent length, and loaded onto a delivery system at least 12 French in size.

EXAMPLE 29

Stents 10 can be fabricated from 24 filament strands of 0.30–0.40 mm diameter PLLA, PDLA, PLLA-PDLA copolymer, 0.35–0.45 mm diameter PGA, PGA-PLLA copolymer, 0.37–0.47 mm diameter PGA-polycaprolactone copolymer, PGA-trimethylcarbonate copolymer, or 0.40–0.50 mm diameter polydioxanone on a 12–18 mm diameter braid mandrel with a filament braid angle of 120–150 degrees while-the braid is on the braid mandrel and annealed on a bar or tube mandrel that has an outer diameter 0.2–10 mm smaller than the braid mandrel diameter at a temperature between the polymer glass-transition temperature and the melting temperature for 5–120 minutes in air, vacuum, or inert atmosphere with the braid in an axially extended, free, or contracted position, cooled to about room temperature, slid off the anneal mandrel, cut to the desired stent length, and loaded onto a delivery system at least 13 French in size.

EXAMPLE 30

Stents 10 can be fabricated from 30 filament strands of 0.30–0.40 mm diameter PLLA, PDLA, PLLA-PDLA copolymer, 0.35–0.45 mm diameter PGA, PGA-PLLA copolymer, 0.37–0.47 mm diameter PGA-polycaprolactone copolymer, PGA-trimethylcarbonate copolymer, or 0.40–0.50 mm diameter polydioxanone on a 16–26 mm diameter braid mandrel with a filament braid angle of 120–150 degrees while the braid is on the braid mandrel and annealed on a bar or tube mandrel that has an outer diameter 0.2–10 mm smaller than the braid mandrel diameter at a temperature between the polymer glass-transition temperature and the melting temperature for 5–120 minutes in air, vacuum, or inert atmosphere with the braid in an axially extended, free, or contracted position, cooled to about room temperature, slid off the anneal mandrel, cut to the desired stent length, and loaded onto a delivery system at least 14 French in size.

EXAMPLE 31

Stents 10 can be fabricated from 36 filament strands of 0.35–0.45 mm diameter PLLA, PDLA, PLLA-PDLA copolymer, 0.40–0.50 mm diameter PGA, PGA-PLLA copolymer, 0.42–0.52 mm diameter PGA-polycaprolactone copolymer, PGA-trimethylcarbonate copolymer, or 0.45–0.55 mm diameter polydioxanone on a 20–30 mm diameter braid mandrel with a filament braid angle of 120–150 degrees while the braid is on the braid mandrel and annealed on a bar or tube mandrel that has an outer diameter 0.2–10 mm smaller than the braid mandrel diameter at a temperature between the polymer glass-transition temperature and the melting temperature for 5–120 minutes in air, vacuum, or inert atmosphere with the braid in an axially extended, free, or contracted position, cooled to about room temperature, slid off the anneal mandrel, cut to the desired stent length, and loaded onto a delivery system at least 18 French in size.

EXAMPLE 32

Stents 10 can be fabricated from 24 filament strands of 0.35–0.45 mm diameter PLLA, PDLA, PLLA-PDLA copolymer, 0.40–0.50 mm diameter PGA, PGA-PLLA copolymer, 0.42–0.52 mm diameter PGA-polycaprolactone copolymer, PGA-trimethylcarbonate copolymer, or 0.45–0.55 mm diameter polydioxanone on a 14–20 mm diameter braid mandrel with a filament braid angle of 126–150 degrees while the braid is on the braid mandrel and annealed on a bar or tube mandrel that has an outer diameter 0.2–10 mm smaller than the braid mandrel diameter at a temperature between the polymer glass-transition temperature and the melting temperature for 5–120 minutes in air, vacuum, or inert atmosphere with the braid in an axially extended, free, or contracted position, cooled to about room temperature, slid off the anneal mandrel, cut to the desired stent length, and loaded onto a delivery system at least 14 French in size.

Figure 4:
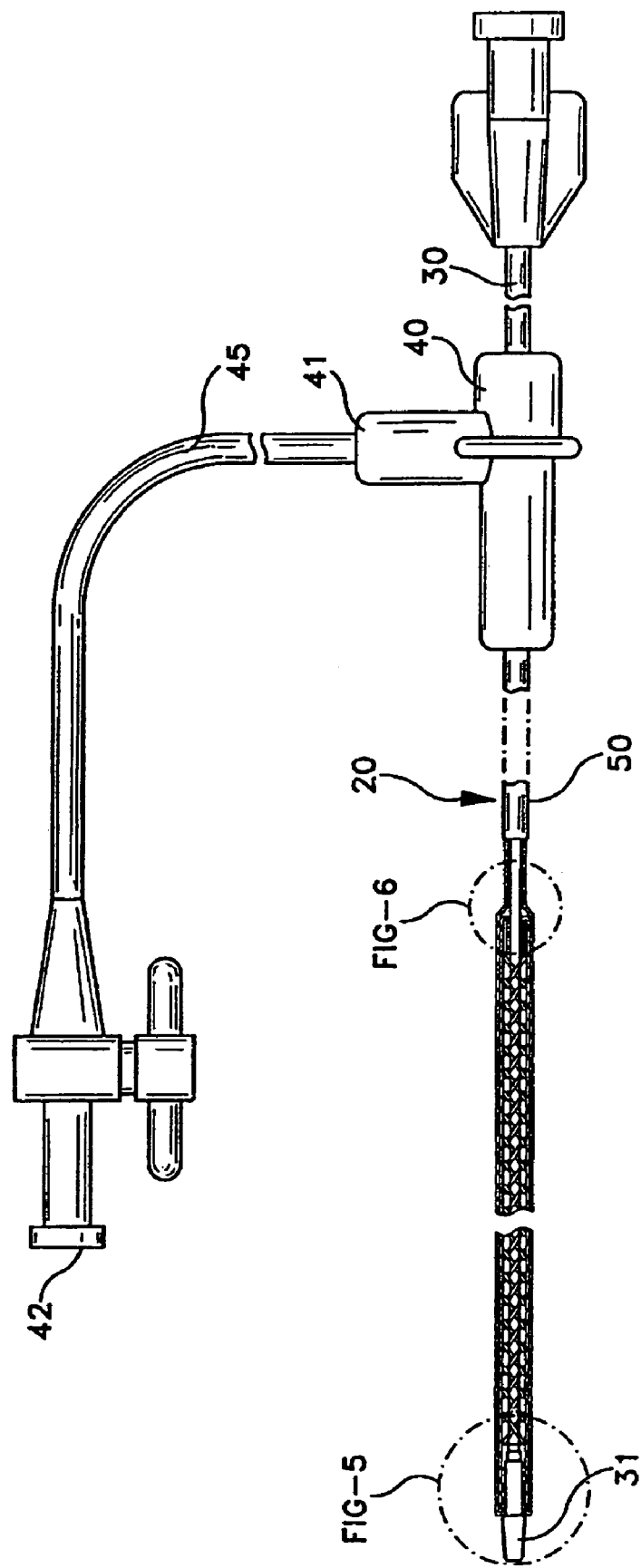
FIG. 4 is a side view of a delivery device with the stent shown in FIG. 1 loaded thereon.
Figure 5:
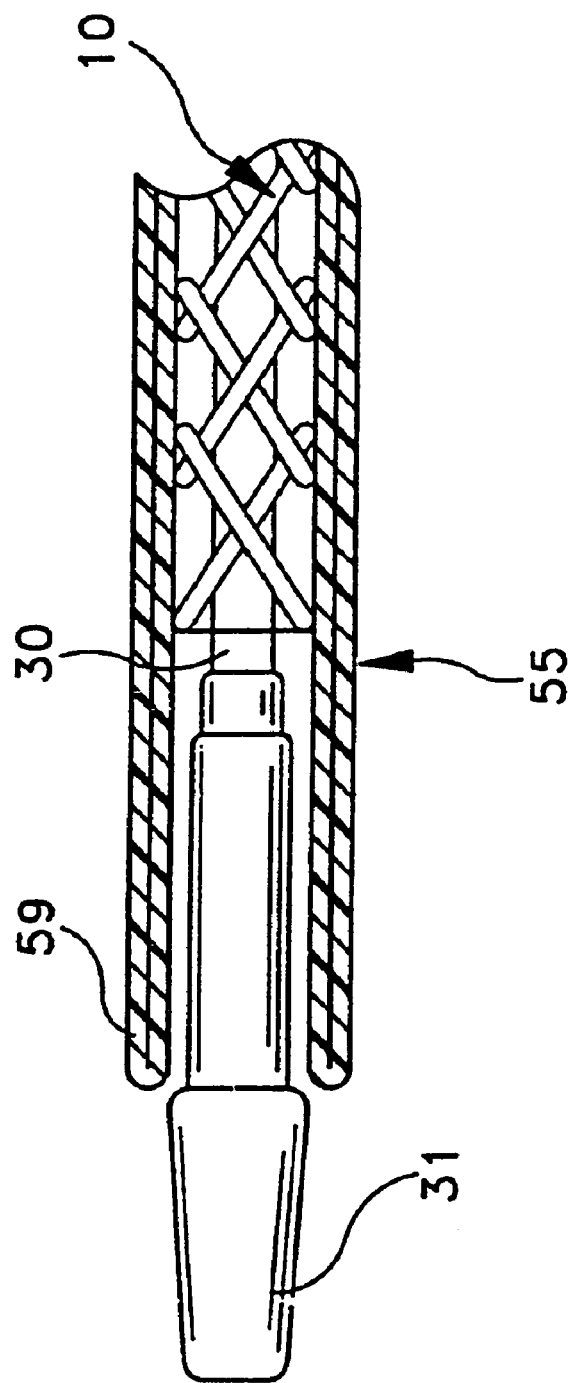
FIG. 5 is a detailed view of the portion of the delivery device encircled at 5 in FIG. 4.
Figure 6:
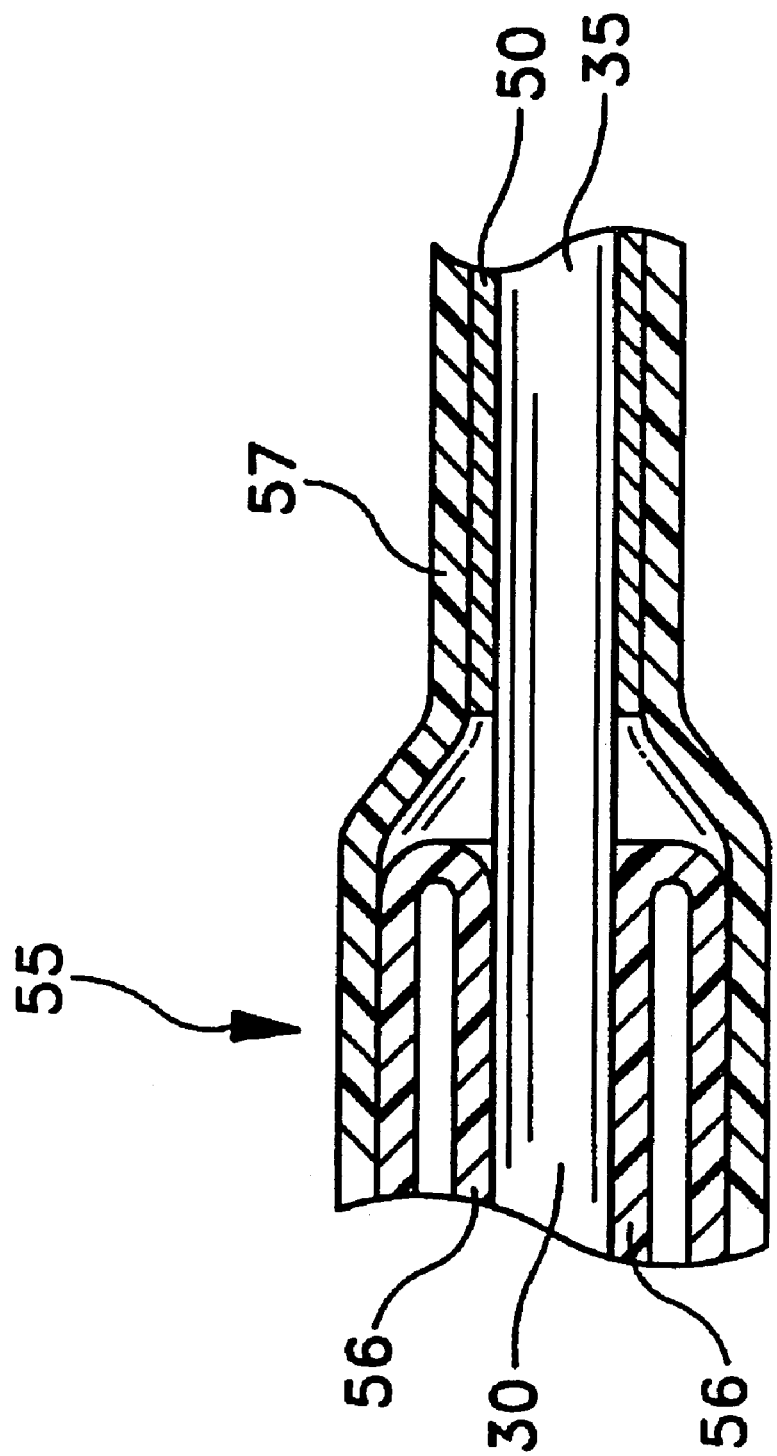
FIG. 6 is a detailed view of the portion of the delivery device encircled at 6 in FIG. 4.
Figure 7:
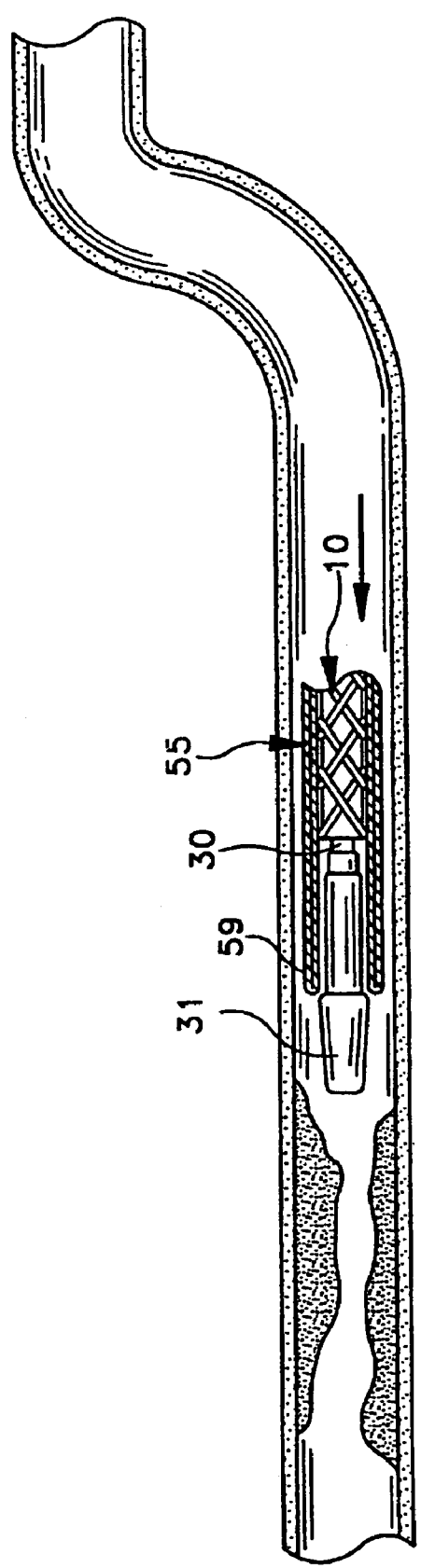
FIGS. 7–10 are partial cross-sectional side views of the distal portion of the delivery device and stent shown in FIG. 4 at various stages during a stent deployment operation in a body vessel.
Figure 8:
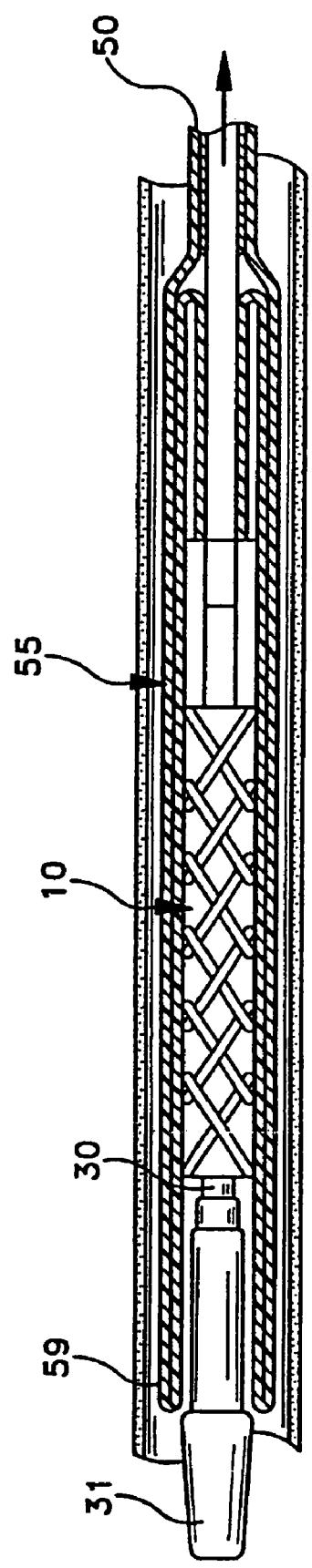
Figure 9:
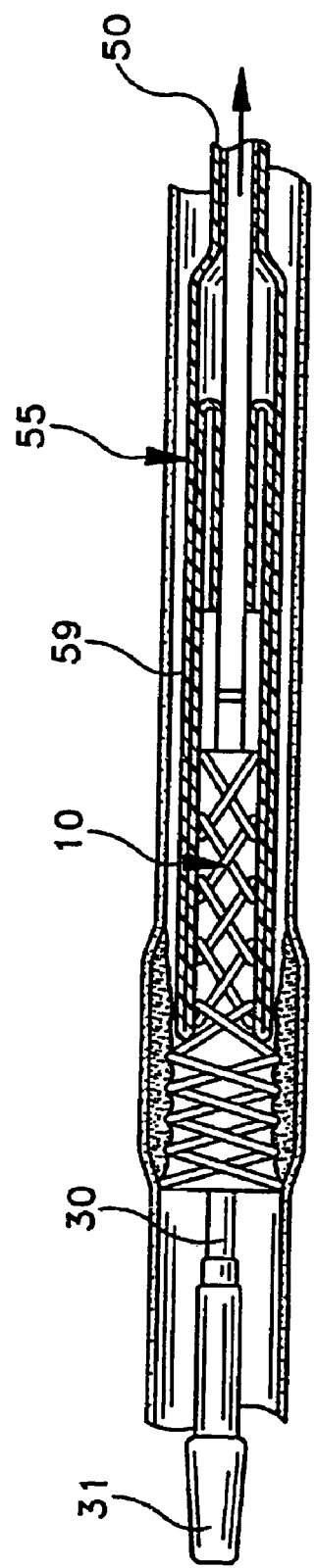
Figure 10:
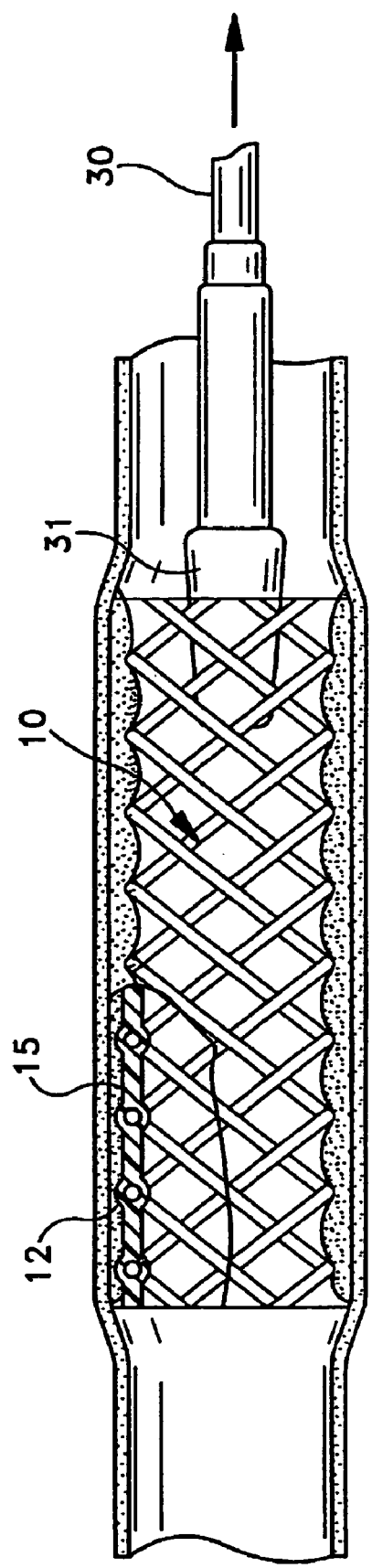

FIGS. 4–6 are illustrations of a coaxial inner/outer tube catheter delivery device 20 for delivering stent 10 to a treatment site in a body vessel. An extension 45 extends from side port 41 to an opening 42.

As shown, stent 10 may be carried by the distal portion of delivery device 20, and is placed on the delivery device in a radially contracted or compressed state. The proximal portion of delivery device 20 generally remains outside of the body for manipulation by the operator.

The manner by which delivery device 20 is operated to deliver stent 10 to a treatment site in a body vessel or lumen including curved sections is illustrated in FIGS. 7–10. As shown, stent 10 is placed in a radially compressed state in a surrounding relationship to the outer distal end of inner tube 30. A tip 31 is disposed at the distal end of tube 30. Stent 10 is constrained on inner tube 30 by the double-walled section of hose 55. It is important that stent 10 not be confined too tightly on inner tube 30. Hose 55 should apply just enough force to stent 10 to hold stent 10 in place. The double-walled section of hose 55 can be removed from around stent 10 by pulling valve body 40 and proximal tube 50 in a proximal direction. The double-walled section "rolls" off stent 10. No sliding movements take place between stent 10 and inner wall 56 which contacts stent 10. Holes 59 are located in the double wall section of the holes 55. Along with the movement of the double-walled section in a proximal direction, the distal end of stent 10 will be exposed in a radial direction to engagement against the wall of the body vessel. As the double-walled section of hose 55 continues moving proximally, more of stent 10 expands in a radial direction until the entire length of stent 10 is exposed and engages the wall of a body vessel.

Lumen 35 is used to enable delivery device 20 to follow a guide wire (not shown) previously inserted percutaneously into the body vessel. The lumen of inner tube 30 can also be used to introduce a contrast fluid to the area around the distal end of delivery device 20 so the position of delivery device 20 can be detected (e.g., through the use of fluoroscopy or X-ray techniques).

The stents of the present invention may be delivered by alternative methods or using alternative devices. For instance, the device described in Heyn et al. U.S. Pat. No. 5,201,757 may be utilized.

FIG. 11 illustrates a delivery device with an outer tube 61 including member 63 and an inner tube 62 including members 64, 65. Stent 10 may be disposed in region 66, and one position of member 65 is shown at about region 67. Member 64 may move in the direction of arrow 68 to push the stent out through end 70 into contact with the interior of wall 72. The stent 10 is shown as lines 69, 71. The end 70 may be moved by moving member 63 in the direction of arrow 73.

Figure 12:
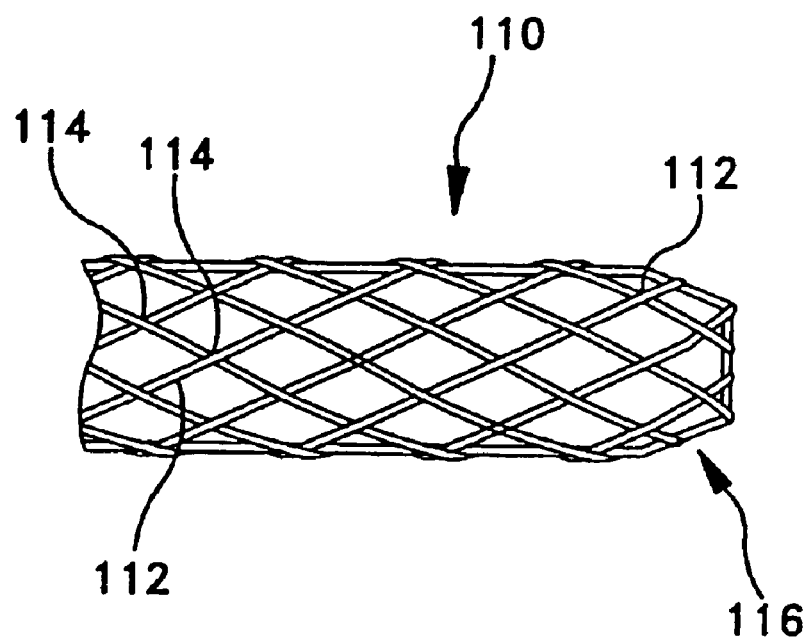
FIG. 12 is a side view of a second embodiment of a stent in accordance with the present invention.

Another embodiment of the present invention, stent 110, is illustrated in FIGS. 12. and 13. Stent 110 is similar to stent 10 described above in that it is a tubular device formed from two sets of oppositely-directed, parallel, spaced-apart and helically wound elongated strands or filaments 112. The sets of filaments 112 are interwoven in an over and under braided configuration intersecting at points such as 114 to form an open mesh or weave construction. One end 116 of stent 110 is tapered and has a diameter which decreases from the diameter of the other portions of the stent to a reduced diameter. Stent 110 can be otherwise identical in structure and fabricated from the same PLLA or absorbable polymer materials as stent 10 described above. Stent 110 can be applied (in the manner of stent 10 described above) to a desired location within a vessel, for example, Vena Cava Inferior, for the purpose of preventing lung emboly. When used in this application, stent 110 can be inserted into Vena Cava with a high degree of precision and functions as a filter.

Stents 10 and 110 offer considerable advantages. In particular, the polymers from which they are formed are highly biocompatible and exhibit good resistance to thrombosis and bacteria adhesion. The stents 10 and 110 have a relatively low elastic modulus, moderately low strength, and high ductility. They are therefore durable yet sufficiently flexible that they can be delivered to treatment sites through curved body vessels. The PLLA stents 10 and 110 may exert a gentler radial force against the lumen wall than would the current Elgiloy® stent. The radial force could be made to be higher or lower by utilizing larger or smaller diameter filament in the stent construction.

Although the present invention has been described with reference to preferred embodiments, those skilled in the art will recognize that changes can be made in form and detail without departing from the spirit and scope of the invention.

It will be evident from considerations of the foregoing that the bioabsorbable self-expanding stent 10 may be constructed using a number of methods and materials, in a wide variety of sizes and styles for the greater efficiency and convenience of a user.

Another bioabsorbable stent that may advantageously be used in conjunction with the present invention is disclosed in J. Stinson's U.S. Pat. No. 5,980,564 entitled "Bioabsorbable Implantable Endoprosthesis With Reservoir And Method Of Using Same", based on application Ser. No. 08/905,806 filed concurrently herewith, and commonly assigned to the assignee of this application.

A bioabsorbable marker that may advantageously be used in conjunction with the present invention is disclosed in J. Stinson's and Claude Clerc's U.S. Pat. No. 6,340,367 entitled "Radiopaque Markers And Methods Of Using Same", based on application Ser. No. 08/905,821, filed concurrently herewith, and commonly assigned to the assignee of this application.

Another bioabsorbable marker that may advantageously be used in conjunction with the present invention is disclosed in J. Stinson's U.S. Pat. No. 6,174,330 entitled "Bioabsorbable Marker Having Radiopaque Constituents And Method Of Using Same", based on application Ser. No. 08/904,951, filed concurrently herewith, and commonly assigned to the assignee of this application.

The above described embodiments of the invention are merely descriptive of its principles and are not to be considered limiting. Further modifications of the invention herein disclosed will occur to those skilled in the respective arts and all such modifications are deemed to be within the scope of the invention as defined by the following claims.

What is claimed is:

1. A prosthesis formed according to a process including:
    braiding a plurality of elongate filaments composed of a bioabsorbable material on a first mandrel to form a tubular, radially compressible prosthesis structure having a first diameter;
    disposing the prosthesis structure on a second mandrel having a second diameter less than the first diameter; and
    while the prosthesis structure is so disposed, annealing the prosthesis structure at a temperature between a glass transition temperature of the bioabsorbable material and a melting temperature of the bioabsorbable material, to form an annealed prosthesis structure having an annealed diameter D when in a free state less than the first diameter of the prosthesis structure before said annealing, the annealed prosthesis structure further being radially compressible to reduced diameters less than the annealed diameter D and radially self-expandable from the reduced diameters;
    wherein the annealed prosthesis structure consists essentially of the elongate filaments.

2. The prosthesis of claim 1 wherein:
    the elongate bioabsorbable filaments comprise a material selected from the group consisting of: polydioxanone, polycaprolactone, polygluconate, polylactic acid-polyethylene oxide copolymers, modified cellulose, collagen, poly(hydroxybutyrate), polyanhydride, polyphosphoester, poly(amino acids), poly-L-lactide, poly-D-lactide, polyglycolide, poly(alpha-hydroxy acid) and combinations thereof.

3. The prosthesis of claim 2 wherein:
    the bioabsorbable material is selected from the group consisting of poly-L-lactide, poly-D-lactide, polyglycolide, and their combinations.

4. The prosthesis of claim 2 wherein:
the filaments consist of polyglycolide.

5. The prosthesis of claim 2 wherein:
the filaments include at least one of the bioabsorbable materials selected from the group consisting of polygluconate and polydioxanone.

6. The prosthesis of claim 1 wherein:
the first diameter is in the range of 3–30 mm, and the annealed diameter D is in the range of 0.2–10 mm.

7. The prosthesis of claim 1 wherein:
the filaments are substantially uniform in cross-section and length.

8. The prosthesis of claim 1 wherein:
the filaments include first and second sets of filaments wound helically in respective and opposite first and second common directions.

9. The prosthesis of claim 8 wherein:
said sets of filaments cross one another at an axially directed angle between about 120 degrees and about 150 degrees.

10. A bioabsorbable implantable annealed prosthesis structure, including:
a first set of flexible bioabsorbable filaments wound helically in a first common direction, and a second set of flexible bioabsorbable filaments wound helically in a second common direction different from the first common direction, crossing the filaments of the first set and cooperating with the first set of filaments to form a prosthesis structure having an initial diameter;
wherein the prosthesis structure is selectively treated according to a process including selecting a diameter D less than the initial diameter and corresponding to a target radial force value according to a relationship, predetermined with respect to an annealed prosthesis structure, between annealed diameter and radial force exerted by the annealed prosthesis structure when radially constrained to a predetermined fraction of the annealed diameter, followed by annealing the prosthesis structure to form an annealed prosthesis structure having the selected diameter D when in a relaxed state;
wherein the annealed prosthesis structure exerts an outwardly directed radial force when radially constrained to diameters less than the selected diameter D, and exerts a radial force substantially equal to said target radial force value when constrained to said predetermined fraction of the selected diameter.

11. The prosthesis of claim 10 wherein:
the elongate bioabsorbable filaments comprise a material selected from the group consisting of: polydioxanone, polycaprolactone, polygluconate, polylactic acid-polyethylene oxide copolymers, modified cellulose, collagen, poly(hydroxybutyrate), polyanhydride, polyphosphoester, poly(amino acids), poly-L-lactide, poly-D-lactide, polyglycolide, poly(alpha-hydroxy acid) and combinations thereof.

12. The prosthesis of claim 11 wherein:
the bioabsorbable material is selected from the group consisting of poly-L-lactide, poly-D-lactide, polyglycolide, and their combinations.

13. The prosthesis of claim 10 wherein:
the filaments consist of polyglycolide.

14. The prosthesis of claim 10 wherein:
the filaments include at least one of the bioabsorbable materials selected from the group consisting of polygluconate and polydioxanone.

15. The prosthesis of claim 10 wherein:
the first diameter is in the range of 3–30 mm, and the second diameter is in the range of 0.2–10 mm.

16. The prosthesis of claim 10 wherein:
the filaments are substantially uniform in cross-section and length.

17. The prosthesis of claim 10 wherein:
the first and second common directions of winding are opposite one another.

18. The prosthesis of claim 17 wherein:
said sets of filaments cross one another at an axially directed angle between about 120 degrees and about 150 degrees.

19. The prosthesis of claim 10 wherein:
the flexible bioabsorbable filaments of the first and second sets are interbraided.

20. A radially self-expanding bioabsorbable prosthesis configured with predetermined radial force characteristics according to a process including:
providing a tubular, radially compressible prosthesis structure composed of a plurality of elongate bioabsorbable filaments and having a first diameter;
selecting a target radial force;
determining an annealed diameter D less than the first diameter and corresponding to the selected target radial force according to a relationship, predetermined with respect to an annealed prosthesis structure, between annealed diameter and radial force exerted by the annealed prosthesis structure when radially compressed to a predetermined fraction of the annealed diameter;
while maintaining the prosthesis structure at the annealed diameter D, annealing the prosthesis structure at a temperature between a glass-transition temperature of the bioabsorbable filaments and a melting temperature of the bioabsorbable filaments, to form an annealed prosthesis structure having the annealed diameter D when in a relaxed state;
wherein the annealed prosthesis structure exerts a radial force when radially compressed to diameters less than the annealed diameter D, and exerts a radial force substantially equal to the selected radial target force when compressed to said predetermined fraction of the annealed diameter D.

21. The prosthesis of claim 20 wherein:
providing the radially compressible stent structure includes winding the plurality of elongate bioabsorbable filaments on a first mandrel; and
maintaining the prosthesis structure at the annealed diameter includes disposing the prosthesis structure on a second mandrel having a diameter less than that of the first mandrel.

22. The prosthesis of claim 20 wherein:
the elongate bioabsorbable filaments comprise a material selected from the group consisting of: polydioxanone, polycaprolactone, polygluconate, polylactic acid-polyethylene oxide copolymers, modified cellulose, collagen, poly(hydroxybutyrate), polyanhydride, polyphosphoester, poly(amino acids), poly-L-lactide, poly-D-lactide, polyglycolide, poly(alpha-hydroxy acid) and combinations thereof.

23. The prosthesis of claim 22 wherein:
the bioabsorbable material is selected from the group consisting of poly-L-lactide, poly-D-lactide, polyglycolide, and their combinations.

24. The prosthesis of claim 20 wherein:
the filaments consist of polyglycolide.

25. The prosthesis of claim 20 wherein:
the filaments include at least one of the bioabsorbable materials selected from the group consisting of polygluconate and polydioxanone.

26. The prosthesis of claim 20 wherein:
the first diameter is in the range of 3–30 mm, and the second diameter is in the range of 0.2–10 mm.

27. The prosthesis of claim 20 wherein:
the filaments are substantially uniform in cross-section and length.

28. The prosthesis of claim 21 wherein:
the filaments are wound in first and second common directions of winding, opposite one another.

29. The prosthesis of claim 17 wherein:
said filaments cross one another at an axially directed angle between about 120 degrees and about 150 degrees.

30. The prosthesis of claim 20 wherein:
the flexible bioabsorbable filaments are interbraided.

* * * * *